United States Patent
Ehnes et al.

(10) Patent No.: US 11,918,498 B2
(45) Date of Patent: Mar. 5, 2024

(54) INTERNAL ILIAC PRESERVATION DEVICES AND METHODS

(71) Applicant: TriVascular, Inc., Santa Rosa, CA (US)

(72) Inventors: Dale L. Ehnes, Forestville, CA (US); Mark Purter, Windsor, CA (US); Mark Geusen, Santa Rosa, CA (US); Kevin Knoll, Santa Rosa, CA (US); Diego Aristizabal, Santa Rosa, CA (US)

(73) Assignee: TriVascular, Inc., Santa Rosa, CA (US)

( * ) Notice: Subject to any disclaimer, the term of this patent is extended or adjusted under 35 U.S.C. 154(b) by 201 days.

(21) Appl. No.: 17/347,206

(22) Filed: Jun. 14, 2021

(65) Prior Publication Data

US 2021/0298931 A1  Sep. 30, 2021

Related U.S. Application Data

(63) Continuation of application No. 15/965,649, filed on Apr. 27, 2018, now Pat. No. 11,033,413, which is a
(Continued)

(51) Int. Cl.
*A61F 2/954* (2013.01)
*A61F 2/82* (2013.01)
*A61F 2/966* (2013.01)

(52) U.S. Cl.
CPC ............ *A61F 2/954* (2013.01); *A61F 2/82* (2013.01); *A61F 2/966* (2013.01)

(58) Field of Classification Search
CPC .... A61F 2/82; A61F 2/95; A61F 2/954; A61F 2/962; A61F 2/966
See application file for complete search history.

(56) References Cited

U.S. PATENT DOCUMENTS 6,224,609 B1  5/2001  Ressemann et al.
6,395,019 B2  5/2002  Chobotov
(Continued)

FOREIGN PATENT DOCUMENTS

EP  1 043 041 A1  10/2000
WO  WO-00/53251 A1  9/2000
(Continued)

OTHER PUBLICATIONS

European Office Action dated Sep. 16, 2021, from application No. 15816618.1.
(Continued)

*Primary Examiner* — Ryan J. Severson
(74) *Attorney, Agent, or Firm* — Foley & Lardner LLP

(57) ABSTRACT

A system for internal iliac preservation includes a catheter having a distal catheter portion and a proximal catheter portion; a first guidewire having a proximal portion extending from the proximal catheter portion, a distal portion and a medial portion disposed between the proximal portion and the distal portion; a first outer sheath slidably disposed over distal catheter portion; and an integrated second delivery system disposed within the outer sheath at the distal catheter portion. The integrated second delivery system includes a second guidewire; an expandable stent-graft disposed over a lumen of the second guidewire, and a slidable connector slidably disposed over the medial portion of the first guidewire, where the second guidewire is slidably engaged with the slidable connection to permit movement of the integrated second delivery system along the first guidewire when the first outer sheath is retracted from distal catheter portion.

20 Claims, 21 Drawing Sheets

Related U.S. Application Data continuation of application No. 14/958,085, filed on Dec. 3, 2015, now Pat. No. 9,956,101.

(60) Provisional application No. 62/087,318, filed on Dec. 4, 2014.

(56) References Cited

U.S. PATENT DOCUMENTS

| | | | |
|---|---|---|---|
| 6,673,103 B1 | 1/2004 | Golds et al. |
| 6,676,691 B1 | 1/2004 | Hosny |
| 6,733,521 B2 | 5/2004 | Chobotov et al. |
| 6,761,733 B2 | 7/2004 | Chobotov et al. |
| 6,776,604 B1 | 8/2004 | Chobotov et al. |
| 7,081,129 B2 | 7/2006 | Chobotov |
| 7,090,693 B1 | 8/2006 | Chobotov et al. |
| 7,125,464 B2 | 10/2006 | Chobotov et al. |
| 7,125,646 B2 | 10/2006 | Mori |
| 7,147,455 B2 | 12/2006 | Chobotov et al. |
| 7,147,660 B2 | 12/2006 | Chobotov et al. |
| 7,147,661 B2 | 12/2006 | Chobotov et al. |
| 7,150,758 B2 | 12/2006 | Kari et al. |
| 7,371,248 B2 | 5/2008 | Dapolito et al. |
| 7,413,573 B2 | 8/2008 | Hartley et al. |
| 7,537,606 B2 | 5/2009 | Hartley et al. |
| 7,645,298 B2 | 1/2010 | Hartley et al. |
| 7,651,071 B1 | 1/2010 | Tanner et al. |
| 7,670,369 B2 | 3/2010 | Schaeffer |
| 7,678,217 B2 | 3/2010 | Chobotov et al. |
| 7,682,475 B2 | 3/2010 | Chobotov et al. |
| 7,766,954 B2 | 8/2010 | Chobotov et al. |
| 7,771,465 B2 | 8/2010 | Zukowski |
| 7,780,717 B2 | 8/2010 | Ducke et al. |
| 7,846,194 B2 | 12/2010 | Hartley et al. |
| 7,914,572 B2 | 3/2011 | Hartley et al. |
| 7,998,186 B2 | 8/2011 | Hartley |
| 7,998,187 B2 | 8/2011 | Hartley et al. |
| 8,012,193 B2 | 9/2011 | Hartley et al. |
| 8,021,412 B2 | 9/2011 | Hartley et al. |
| 8,021,419 B2 | 9/2011 | Hartley et al. |
| 8,043,363 B2 | 10/2011 | Schaeffer |
| 8,080,049 B2 | 12/2011 | Zukowski et al. |
| 8,118,854 B2 | 2/2012 | Bowe |
| 8,167,926 B2 | 5/2012 | Hartley et al. |
| 8,167,927 B2 | 5/2012 | Chobotov |
| 8,262,718 B2 | 9/2012 | Chuter et al. |
| 8,267,988 B2 | 9/2012 | Hamer et al. |
| 8,273,115 B2 | 9/2012 | Hamer et al. |
| 8,353,943 B2 | 1/2013 | Kuppurathanam et al. |
| 8,361,134 B2 | 1/2013 | Hartley et al. |
| 8,394,136 B2 | 3/2013 | Hartley et al. |
| 8,414,636 B2 | 4/2013 | Nabulsi et al. |
| 8,449,600 B2 | 5/2013 | Hartley et al. |
| 8,470,018 B2 | 6/2013 | Hartley et al. |
| 8,475,514 B2 | 7/2013 | Hartley et al. |
| 8,480,726 B2 | 7/2013 | Cunningham et al. |
| 8,523,933 B2 | 9/2013 | Nabulsi et al. |
| 8,545,549 B2 | 10/2013 | Hartley et al. |
| 8,574,288 B2 | 11/2013 | Hartley et al. |
| 8,579,959 B2 | 11/2013 | Ducke et al. |
| 8,636,789 B2 | 1/2014 | Ivancev et al. |
| 8,663,306 B2 | 3/2014 | Kasprzak et al. |
| 8,672,993 B2 | 3/2014 | Chuter et al. |
| 8,702,786 B2 | 4/2014 | Roeder et al. |
| 8,709,061 B2 | 4/2014 | Greenberg et al. |
| 8,728,372 B2 | 5/2014 | Humphrey et al. |
| 8,734,501 B2 | 5/2014 | Hartley et al. |
| 8,740,966 B2 | 6/2014 | Brocker et al. |
| 8,753,385 B2 | 6/2014 | Hartley et al. |
| 8,753,386 B2 | 6/2014 | Shaw |
| 8,771,336 B2 | 7/2014 | Roeder |
| 8,795,349 B2 | 8/2014 | Huser et al. |
| 8,808,349 B2 | 8/2014 | Chuter et al. |
| 8,808,351 B2 | 8/2014 | Osborne |
| 8,808,355 B2 | 8/2014 | Barrand |
| 8,840,657 B2 | 9/2014 | Hartley |
| 8,845,708 B2 | 9/2014 | Hartley et al. |
| 8,864,812 B2 | 10/2014 | Zukowski |
| 8,864,819 B2 | 10/2014 | Hartley et al. |
| 8,870,939 B2 | 10/2014 | Roeder et al. |
| 9,066,828 B2 | 6/2015 | Geusen |
| 9,956,101 B2 | 5/2018 | Ehnes et al. |
| 2001/0007954 A1 | 7/2001 | Shaolian et al. |
| 2005/0158272 A1 | 7/2005 | Whirley et al. |
| 2006/0095118 A1 | 5/2006 | Hartley |
| 2006/0222596 A1 | 10/2006 | Askari et al. |
| 2007/0167913 A1 | 7/2007 | Elkins et al. |
| 2009/0099649 A1 | 4/2009 | Chobotov et al. |
| 2010/0063578 A1 | 3/2010 | Ren et al. |
| 2013/0261734 A1 | 10/2013 | Young et al. |
| 2013/0338752 A1 | 12/2013 | Geusen et al. |
| 2013/0338753 A1 | 12/2013 | Geusen |
| 2013/0338760 A1 | 12/2013 | Aristizabal et al. |
| 2014/0277330 A1 | 9/2014 | Roeder |
| 2015/0012080 A1 | 1/2015 | Barrand |
| 2015/0018932 A1 | 1/2015 | Buddery et al. |

FOREIGN PATENT DOCUMENTS

| | | | |
|---|---|---|---|
| WO | WO-02/083038 A2 | 10/2002 |
| WO | WO-2008/142696 A1 | 11/2008 |
| WO | WO-2010/064244 A2 | 6/2010 |

OTHER PUBLICATIONS

Japanese Office Action dated Nov. 18, 2019, from application No. 2017-529719.

Japanese Office Action dated Oct. 5, 2020, from application No. 2017-529719.

Final Office Action dated Sep. 2, 2020, from U.S. Appl. No. 15/965,649.

International Search Report and Written Opinion for PCT/US2015/063686, dated Mar. 4, 2016.

Non-Final Office Action dated Apr. 23, 2020, from U.S. Appl. No. 15/965,649.

Non-final Office Action dated Nov. 2, 2017, from U.S. Appl. No. 14/958,085.

Notice of Allowance dated Feb. 12, 2021, from U.S. Appl. No. 15/965,649.

U.S. Notice of Allowance dated Dec. 26, 2017, from U.S. Appl. No. 14/958,085.

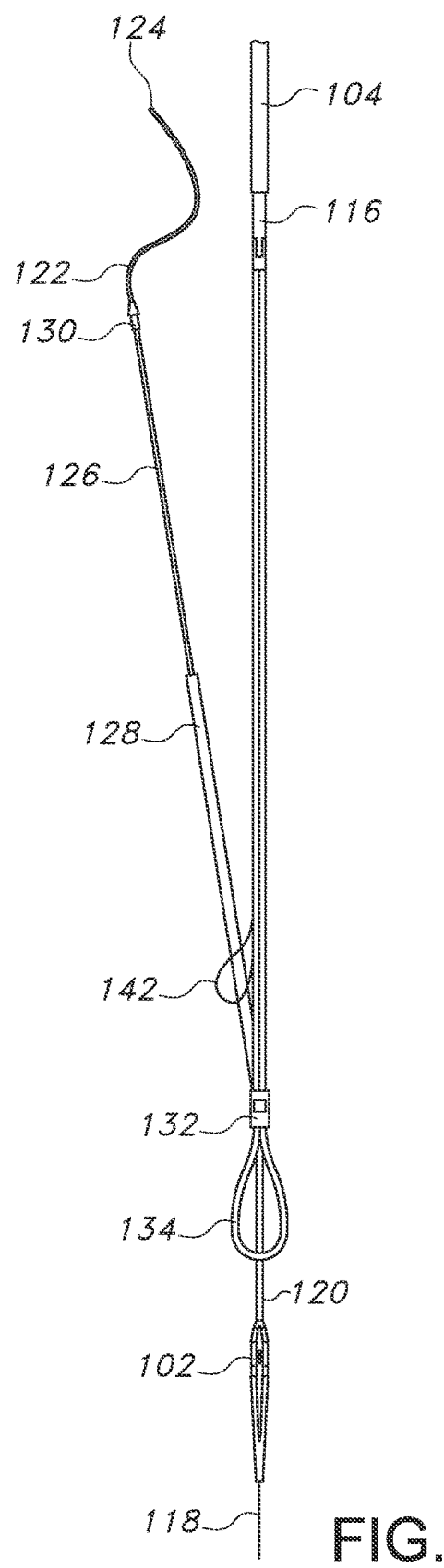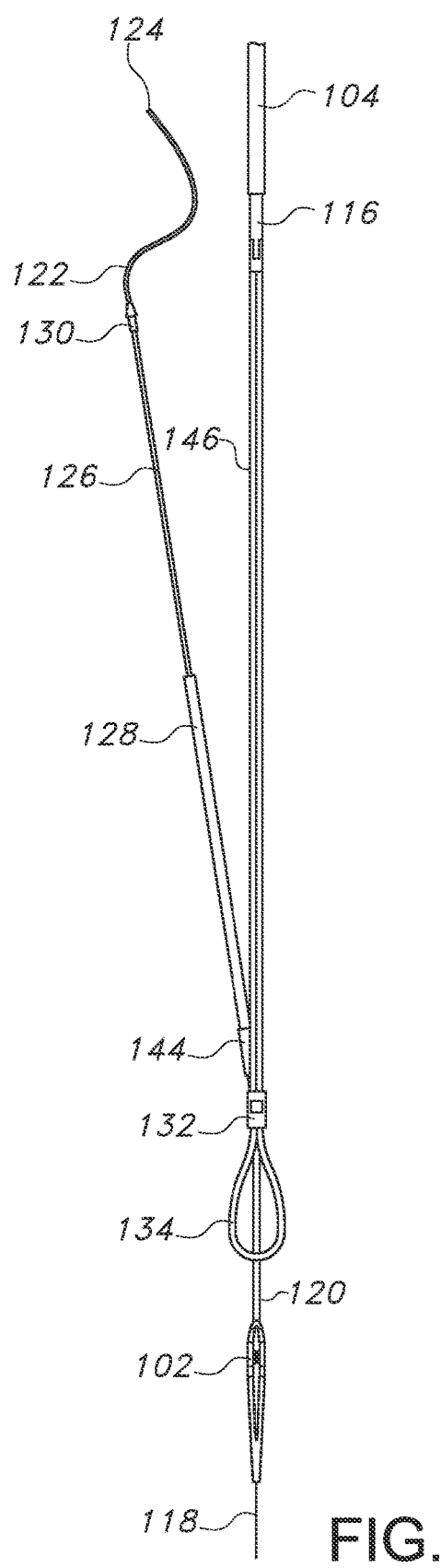

INTERNAL ILIAC PRESERVATION DEVICES AND METHODS

CROSS-REFERENCE TO RELATED APPLICATIONS

This application is a continuation of U.S. patent application Ser. No. 15/965,649, filed Apr. 27, 2018, which is a continuation of U.S. patent application Ser. No. 14/958,085, filed Dec. 3, 2015, now U.S. Pat. No. 9,956,101, granted May 1, 2018, which claims the benefit of U.S. Provisional Application No. 62/087,318, filed Dec. 4, 2014, the contents of which are incorporated by reference herein.

FIELD OF THE INVENTION

The present invention is directed to internal iliac preservation devices and methods. More particularly, the present invention is directed to devices and methods for treating iliac aneurysms while preserving or maintaining blood flow in nearby branched arteries, such as internal iliac or hypogastric arteries. The iliac aneurysms may be treated in conjunction with the treatment of abdominal aortic aneurysms (AAA).

BACKGROUND OF THE INVENTION

Patients with an abdominal aortic aneurysm may also have one or more aneurysms in their (internal and/or external) iliac arteries. Other patients may experience one or more iliac artery aneurysms without having an abdominal aortic aneurysm. Treatment of iliac aneurysms with non-inflatable devices or prostheses, such as but not limited to textile or extruded grafts and/or stent-grafts, typically with an integral or modular stent, currently can require two access points on each of the patient's legs to bring a guidewire up and over the aortic bifurcation and also can require three guidewires to deploy a prosthesis at the iliac aneurysm.

SUMMARY OF THE INVENTION

The present invention preserves blood flow through an internal iliac artery while excluding an iliac aneurysm. The devices of the present invention are deployable from a single access site in the femoral artery to access and treat the internal iliac with a stent-graft. The stent-graft may be a self-expanding stent-graft or it may be a balloon-expandable stent-graft.

Moreover, devices, systems, methods and techniques of the present invention will preserve pelvic perfusion through the internal iliac artery, also referred to as the hypogastric artery, while excluding aneurysmal vessels in surrounding regions.

The devices, systems, methods and techniques of the present invention will preserve flow to the hypogastric artery. This is achieved by, inter alia, sealing the device of the present invention to a healthy portion of a vessel while excluding an aneurysm. As a patient's vasculature is quite complex, one advantage of the devices, systems, methods and techniques of the present invention is that they are easy to use and employ by a practitioner, including ease of approach, access, steering and torque. Moreover, the present invention addresses defined vasculature targets for diameter, radial force and coverage lengths. Furthermore, devices of the present invention may be sandwiched; i.e., employ a modular design with two or more devices being sealingly deployed within the vasculature.

A deployment sequence for the devices and systems of the present invention may include:

1) Gain vasculature access by traditional (cut-down or percutaneous) means.
2) Deploy a main body AAA device and iliac limb to be superior to diseased iliac bifurcation.
3) Position internal iliac device over main guidewire and slide into position such that an expandable stent-graft (either self-expandable or balloon expandable) is superior to the diseased iliac bifurcation.
4) Unsheathe the device and cannulate internal iliac with internal iliac cannulation wire.
5) Once wire access is achieved, position a stent-graft within the internal iliac lumen and expand the stent or stent-graft into position.
6) Advance a catheter proximally until the cannulation wire and associated delivery members are back into the common iliac artery.
7) Re-sheath the internal iliac device and retract the system from the vasculature.
8) Deploy an iliac limb at a matched height to the internal iliac stent-graft and expand the iliac limb as necessary to provide perfusion to both iliac branches. If desired, a balloon may be used with a balloon expandable or a self-expandable iliac limb.

These and other features and advantages of the present invention will become apparent from the following detailed description of illustrative embodiments thereof, which is to be read in connection with the accompanying drawings. Corresponding reference element numbers or characters indicate corresponding parts throughout the several views of the drawings.

BRIEF DESCRIPTION OF THE DRAWINGS

FIGS. 12 and 13 depict additional embodiments for recapture of a delivery sheath of the internal iliac portion of the delivery system.

DETAILED DESCRIPTION OF THE INVENTION

With regard to graft, stent or stent-graft embodiments discussed herein and components thereof, the term "proximal" refers to a location towards a patient's heart and the term "distal" refers to a location away from the patient's heart. With regard to delivery systems, catheters and components thereof discussed herein, the term "distal" refers to a location that is disposed away from an operator who is using the delivery system or catheter and the term "proximal" refers to a location towards the operator.

Figure 1:
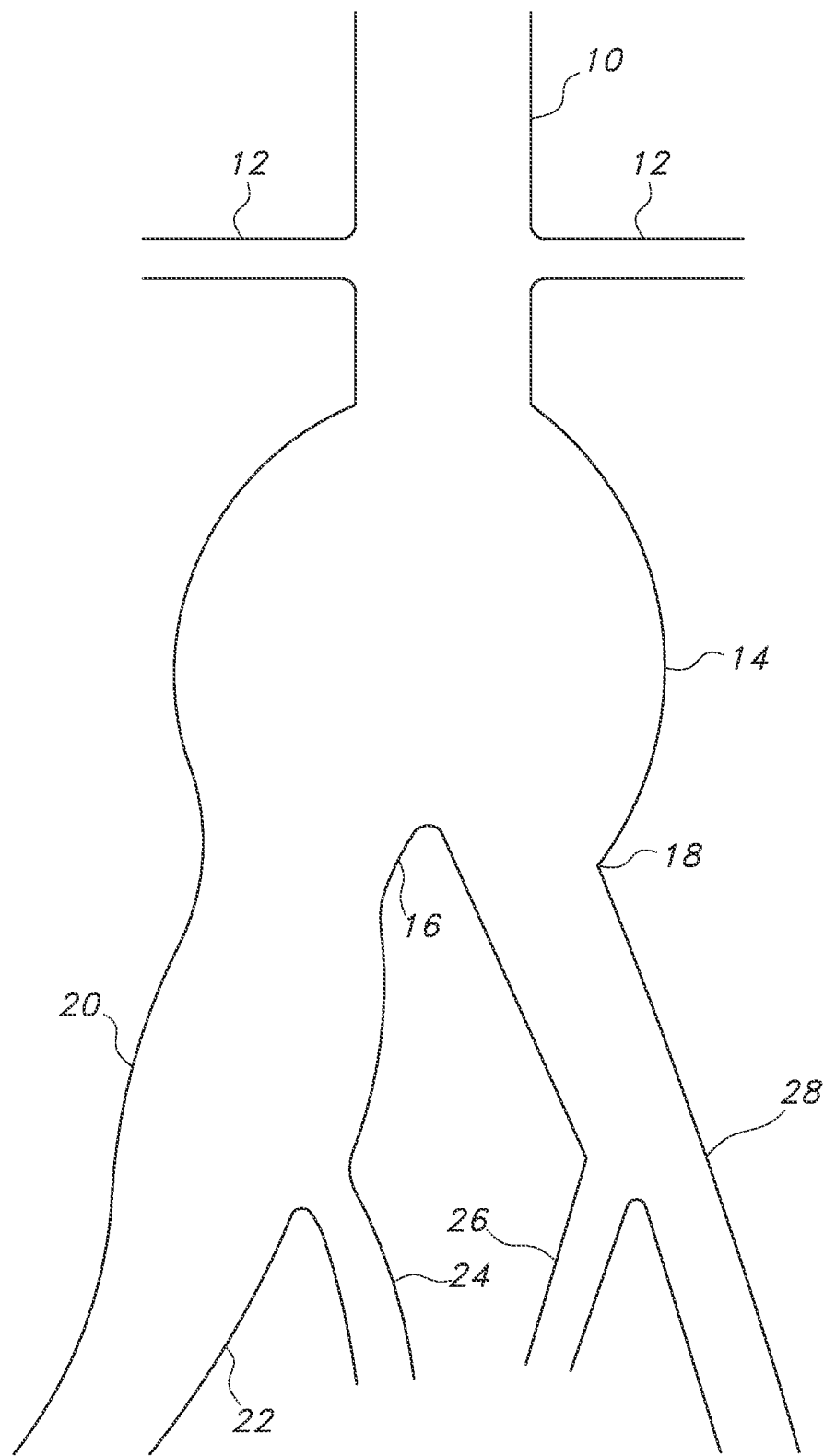
FIG. 1 depicts a portion of a patient's vasculature having an abdominal aortic aneurysm and an iliac aneurysm.

FIG. 1 depicts a portion of a patient's vasculature. An abdominal aortic aneurysm (AAA) 14, if any, may be present within an aorta 10 of a patient. Such an aortic aneurysm is typically below (i.e., in the direction of the patient's feet) the renal arteries 12. About forty percent of patients who have an aortic aneurysm 14 may also have iliac aneurysm 20. The aorta 10 branches into iliac arteries 16, 18. While the iliac arteries 16, 18 may be medically described as the right and left common iliac arteries, respectively, as used herein the iliac artery 16 is sometimes described as an ipsilateral iliac artery and the iliac artery 18 is sometimes described as a contralateral iliac artery. Iliac artery 16 further branches into an external iliac artery 22 and an internal iliac artery or hypogastric artery 24. In a similar fashion, iliac artery 18 also branches into an external iliac artery 28 and an internal iliac artery or hypogastric artery 26. While only iliac artery 16 is depicted as having an iliac aneurysm 20, such an aneurysm may be present in the iliac aneurysm 20 instead of the iliac artery 16.

Figure 2:
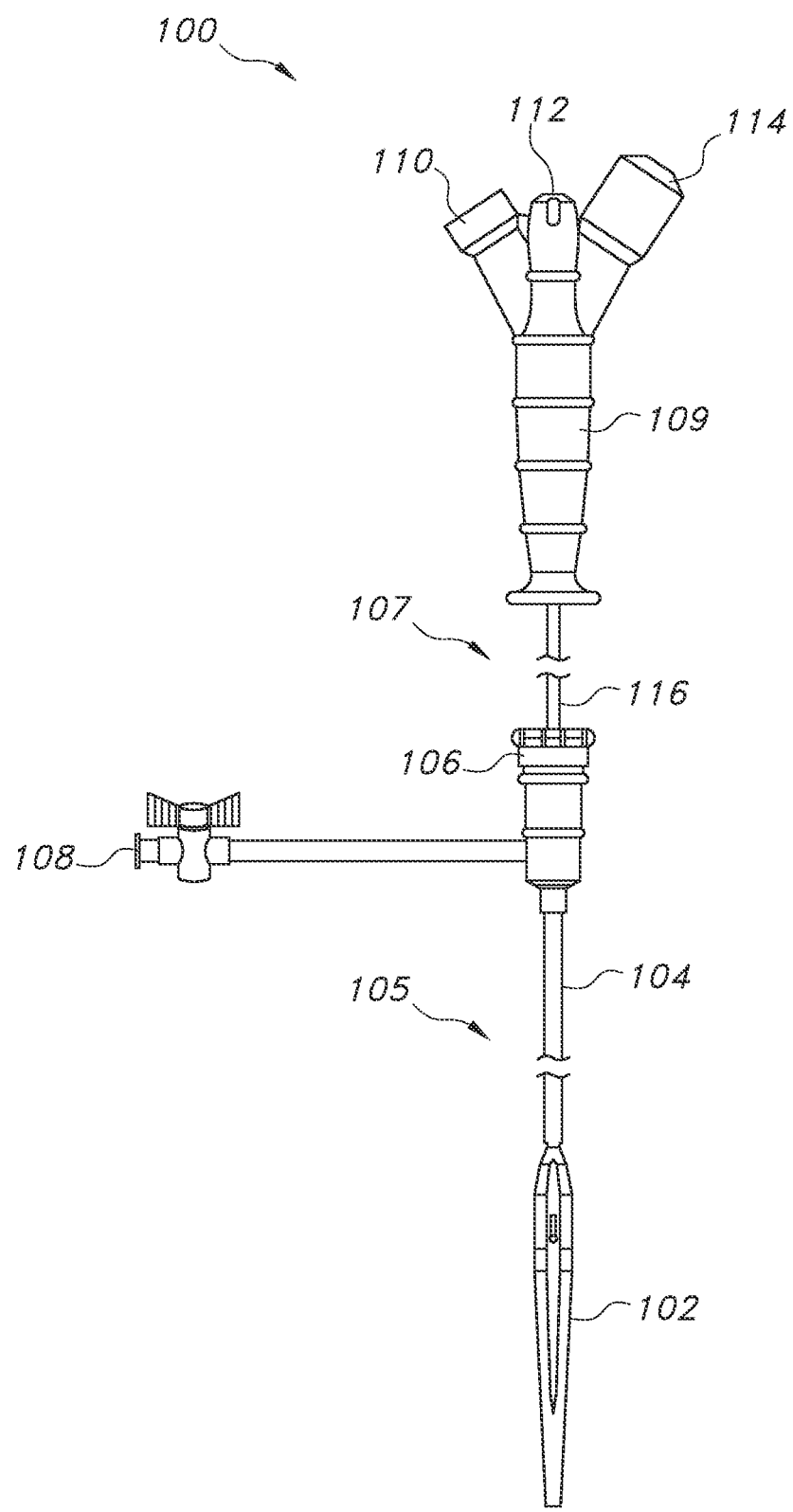
FIG. 2 depicts an embodiment of a delivery system or catheter according to the present invention for treating an iliac aneurysm and for preserving blood flow through an internal iliac artery in an initial delivery configuration.

FIG. 2 depicts a delivery system or catheter 100 of the present invention. As depicted in FIG. 2, the delivery system or catheter 100 may include a distal tip or nosecone 102, an outer sheath 104, a retraction handle 106, an inner tubular member or hypotube 116 and a proximal handle assembly 109. The system or catheter 100 may include a flush port 108 for flushing the outer sheath 104 during delivery stages. The outer sheath 104 may have a radiopaque marker band (not shown) to aid the practitioner in properly navigating the delivery system 100 to the desired bodily site. The outer sheath 104 is retractable by movement of the retraction knob or handle 106 for the outer sheath 104 by a practitioner towards the proximal handle assembly 109 of the delivery system 100. The inner tubular member or hypotube 116 is disposed from the proximal handle assembly 109 along a proximal portion 107 of the delivery system 100 towards a distal portion 105 of the delivery system 100. Further details of the hypotube 116 are disclosed in commonly owned U.S. Pat. No. 9,066,828, the contents of all of which are incorporated by reference herein in their entirety. Further details, including but not limited to methods, catheters and systems, for deployment of endovascular prostheses are disclosed in commonly owned U.S. Pat. Nos. 6,761,733 and 6,733,521 and commonly owned U.S. Patent Application Publication Nos. 2006/0009833 and 2009/0099649, all of which are incorporated by reference herein in their entirety.

The outer sheath 104 may be formed of a biocompatible material. In some embodiments, the biocompatible material may be a biocompatible polymer. Examples of suitable biocompatible polymers may include, but are not limited to, polyolefins such as polyethylene (PE), high density polyethylene (HDPE) and polypropylene (PP), polyolefin copolymers and terpolymers, polytetrafluoroethylene (PTFE), polyethylene terephthalate (PET), polyesters, polyamides, polyurethanes, polyurethaneureas, polypropylene and, polycarbonates, polyvinyl acetate, thermoplastic elastomers including polyether-polyester block copolymers and polyamide/polyether/polyesters elastomers, polyvinyl chloride, polystyrene, polyacrylate, polymethacrylate, polyacrylonitrile, polyacrylamide, silicone resins, combinations and copolymers thereof, and the like. In some embodiments, the biocompatible polymers include polypropylene (PP), polytetrafluoroethylene (PTFE), polyethylene terephthalate (PET), high density polyethylene (HDPE), combinations and copolymers thereof, and the like. Useful coating materials may include any suitable biocompatible coating. Non-limiting examples of suitable coatings include polytetrafluoroethylene, silicone, hydrophilic materials, hydrogels, and the like. Useful hydrophilic coating materials may include, but are not limited to, alkylene glycols, alkoxy polyalkylene glycols such as methoxypolyethylene oxide, polyoxyalkylene glycols such as polyethylene oxide, polyethylene oxide/polypropylene oxide copolymers, polyalkylene oxide-modified polydimethylsiloxanes, polyphosphazenes, poly(2-ethyl-2-oxazoline), homopolymers and copolymers of (meth) acrylic acid, poly(acrylic acid), copolymers of maleic anhydride including copolymers of methylvinyl ether and maleic acid, pyrrolidones including poly(vinylpyrrolidone) homopolymers and copolymers of vinyl pyrrolidone, poly (vinylsulfonic acid), acryl amides including poly(N-alkylacrylamide), poly(vinyl alcohol), poly(ethyleneimine), polyamides, poly(carboxylic acids), methyl cellulose, carboxymethylcellulose, hydroxypropyl cellulose, polyvinylsulfonic acid, water soluble nylons, heparin, dextran, modified dextran, hydroxylated chitin, chondroitin sulphate, lecithin, hyaluranon, combinations and copolymers thereof, and the like. Non-limiting examples of suitable hydrogel coatings include polyethylene oxide and its copolymers, polyvinylpyrrolidone and its derivatives; hydroxyethylacrylates or hydroxyethyl(meth)acrylates; polyacrylic acids; polyacrylamides; polyethylene maleic anhydride, combinations and copolymers thereof, and the like. In some embodiments, the outer sheath 104 may be made of polymeric materials, e.g., polyimides, polyester elastomers (Hytrel®), or polyether block amides (Pebax®), polytetrafluoroethylene, and other thermoplastics and polymers. The outside diameter of the outer sheath 104 may range from about 0.1 inch to about 0.4 inch. The wall thickness of the outer sheath 104 may range from about 0.002 inch to about 0.015 inch. The outer sheath 104 may also include an outer hydrophilic coating. Further, the outer sheath 104 may include an internal braided or otherwise reinforced portion of either metallic or polymeric filaments.

The proximal handle assembly 109 may include a retraction handle 106 may include a main guidewire port 114, an auxiliary port 112 and a secondary guidewire port 110. Any of these ports may further include flushing ports (not shown) or additional nested ports (not shown) having access to, for example, pull or push wires, rods or threads.

Figure 3:
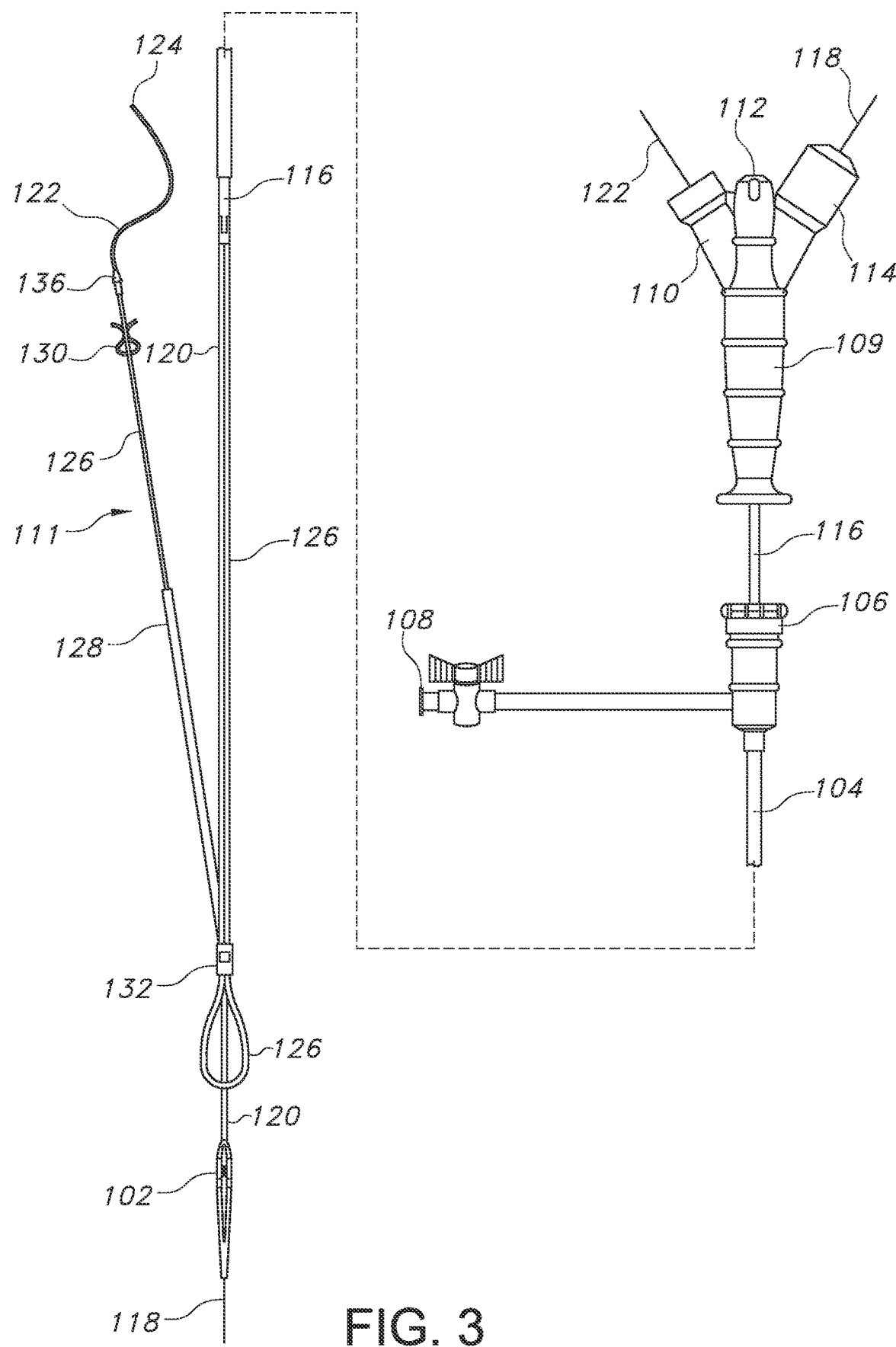
FIG. 3 depicts the delivery system or catheter of FIG. 2 in a deployment configuration.

The delivery system or catheter 100, as depicted in FIG. 2, is in its fully sheathed stage; i.e., the retraction handle 106 is in a distal position and the outer sheath 104 is fully deployed in its distal position. In FIG. 3, the retraction handle 106 has been retracted proximally to retract the outer sheath 104 proximally.

As depicted in FIG. 3, the delivery system or catheter 100 may further include a main guidewire lumen 120 having a main guidewire 118 slidably disposed therein. A distal portion of the main guidewire 118 may exit the distal tip or nosecone 102, and a proximal portion of the main guidewire 118 may be accessed or manipulated via the main guidewire port 114. The main guidewire 118 may typically be deployed into the aortic artery 12 and past the aortic aneurysm 14, if any.

The delivery or catheter system 100 may include an integrated second or hypogastric delivery system or catheter 111. The integrated hypogastric delivery system 111 may include an internal iliac (hypogastric) cannulate wire 122 having a distal end 124, a cannulate wire lumen 126 through which the cannulate wire is slidably disposed therethrough, a second outer sheath 128, a second nosecone 136 and optionally a stent securement component 130 for securing an endovascular prosthesis or stent-graft (not shown), interrelated as shown. The second outer sheath 128 may comprise any of the above-described materials for the outer sheath 104. In FIG. 3, the second outer sheath 128 is in its proximal position for deployment of the stent-graft (not shown). As described below, the second outer sheath 128 is initially positioned proximally to cover the stent-graft. The stent securement component 130 serves to releasably secure the stent-graft within integrated hypogastric delivery system 111 as the second outer sheath 128 is advanced distally to deploy the stent-graft. In other words, the stent securement component 130 is useful for keeping the stent-graft in a relatively fixed position over the cannulate wire lumen 126 as the second outer sheath 128 is retracted or moved proximally.

Figure 4:
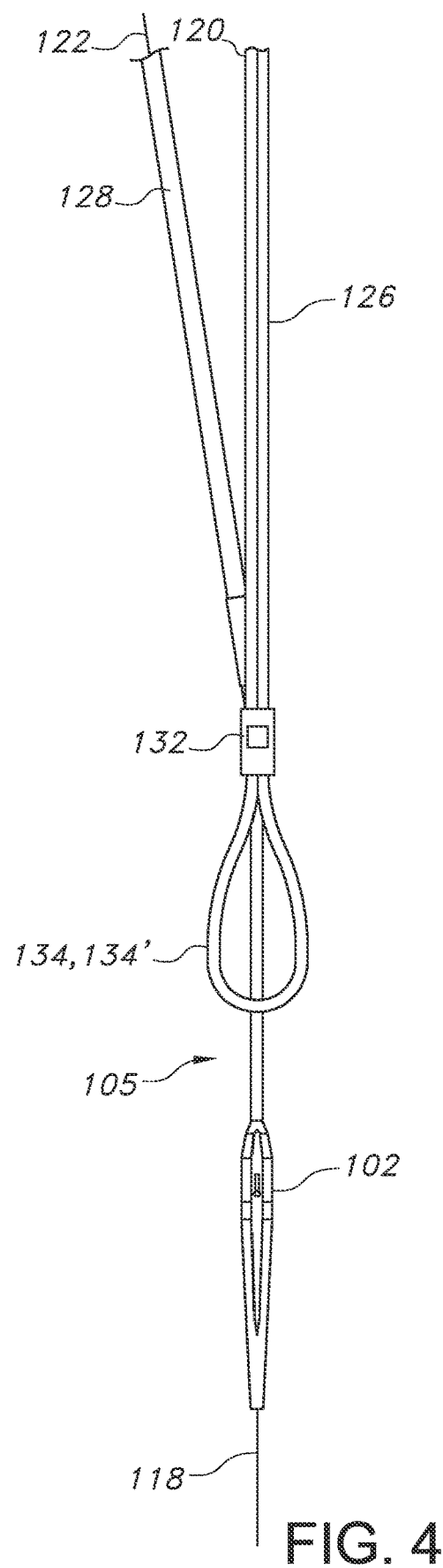
FIG. 4 depicts an embodiment of a distal portion of the delivery system or catheter of FIG. 2 showing a looped lumen portion for an internal iliac cannulation guidewire.

FIG. 4 is an exploded of a distal portion of delivery system of catheter of FIG. 3. The cannulate wire 122 is slidably engaged with the main guidewire 118 via a slidable connection 132. Use of the system 100 with such a slidable connection 132 allows for easy positioning and rotation, if required, of the distal portion of the cannulate wire 122 into the internal iliac artery or hypogastric artery 24.

The main guidewire 118 and the cannulate wire 122 are slidably disposed through the slidable connection 132. A portion of the cannulate wire 122 disposed distally past the slidable connection 132 may be, if desired, in the form of a loop 134. The present invention, however, is not so limited, and other arrangements may suitably be used. For example, the delivery system or catheter 100 may include a guidewire-compatible lumen 134' for slidably securing loop 134 of the cannulate wire 122. The slidable connection 132 is movable along the main guidewire lumen 120 or main guidewire 118 for ease of access into the internal iliac artery or hypogastric artery 24. The guidewire shafts or lumens may be a polymeric or metallic member, including but not limited to a hypotube.

Figure 5:
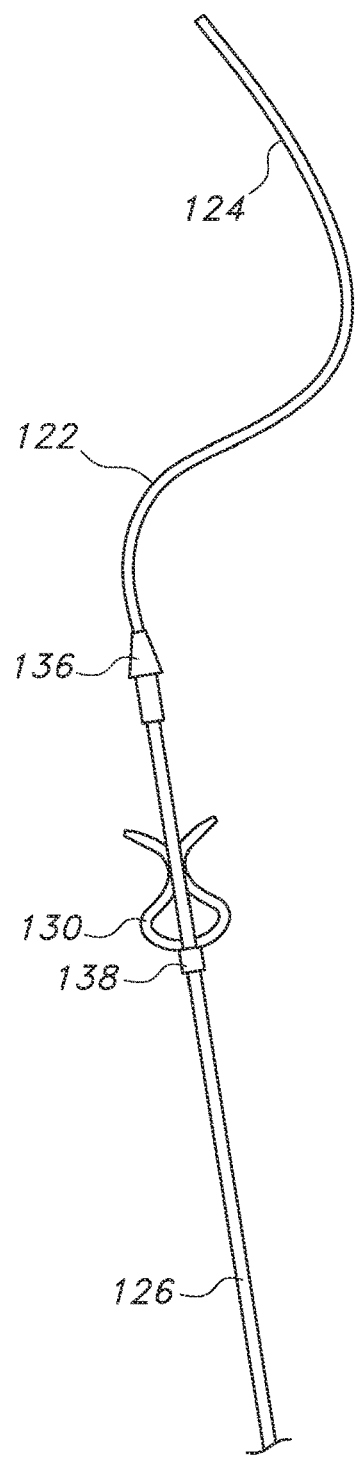
FIG. 5 is an exploded view of a distal portion of the delivery system or catheter of FIG. 2 which is deployable through an internal iliac.
Figure 6:
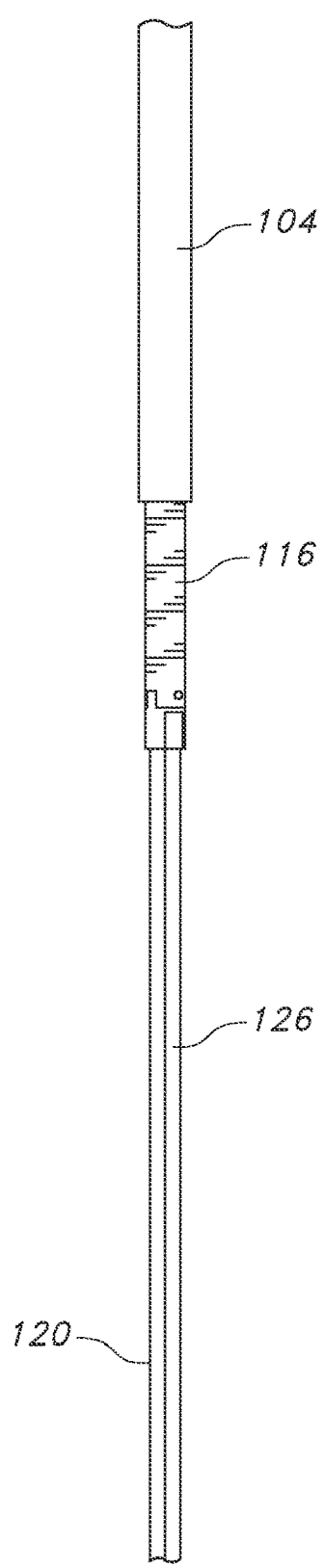
FIG. 6 is an exploded view of a portion of the delivery system or catheter of FIG. 2 showing a hypotube slidably deployable within an outer sheath.

As depicted in FIG. 5, the stent securement component 130 may be secured to the cannulate wire lumen 126 via a stent securement component coupling 138. One non-limiting means for securing the coupling 138 to the lumen 126 may include the use of an adhesive. As depicted in FIG. 6, the outer sheath 104 is retractable over the hypotube 116 during delivery stages with the present invention.

Figure 7:
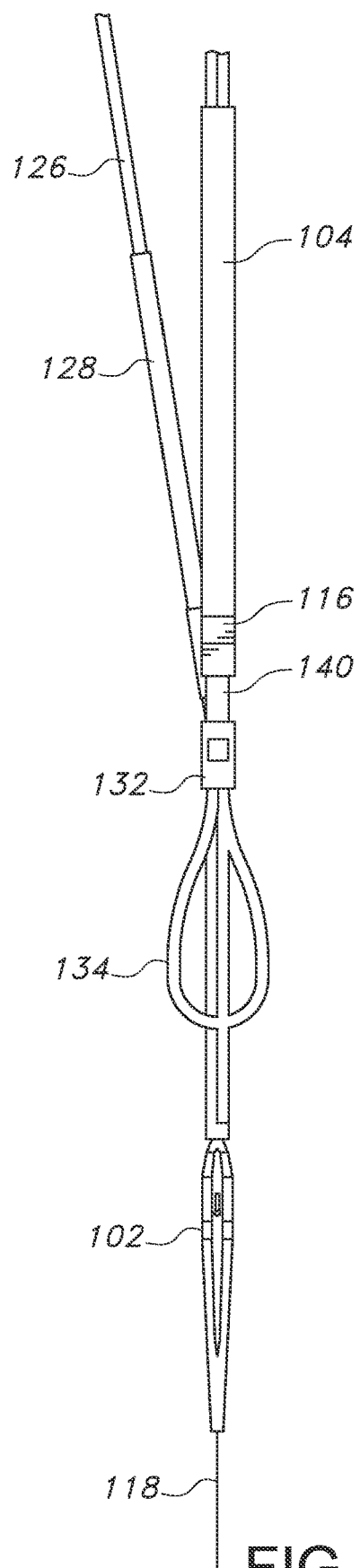
FIG. 7 depicts an embodiment of a distal portion of the delivery system or catheter of FIG. 2 showing a looped lumen portion for an internal iliac cannulation guidewire and a slidable connection for an internal iliac delivery sheath.
Figure 9:
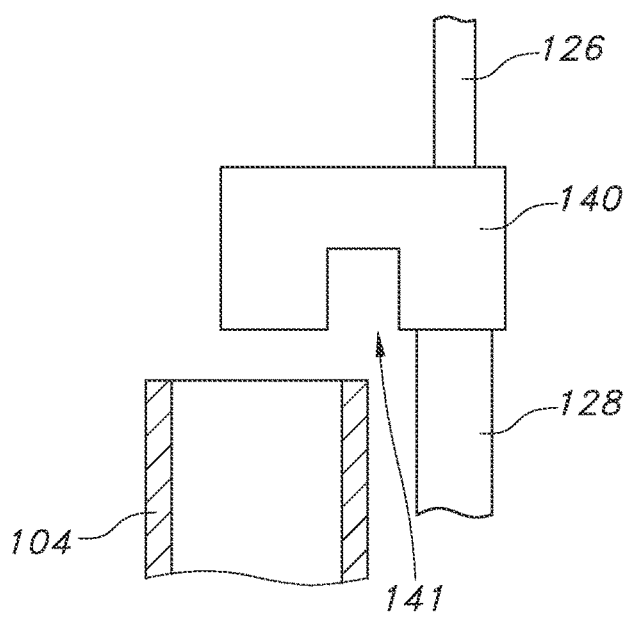

As depicted in FIG. 7, the integrated hypogastric delivery system 111 may include a sheath coupling 140. The sheath coupling 140 is secured to a distal portion of the second outer sheath 128 and is slidably disposed over the cannulate wire lumen 126. The outer sheath 104 may be advanced distally to push the second outer sheath 128 distally to uncover the stent-graft disposed over the cannulate wire lumen 126. As depicted in FIG. 9, the sheath coupling 140 may include a detent 141 which is engagable with an end portion of the outer sheath 104 to facilitate controlled movement of the sheath coupling 140.

Figure 8:
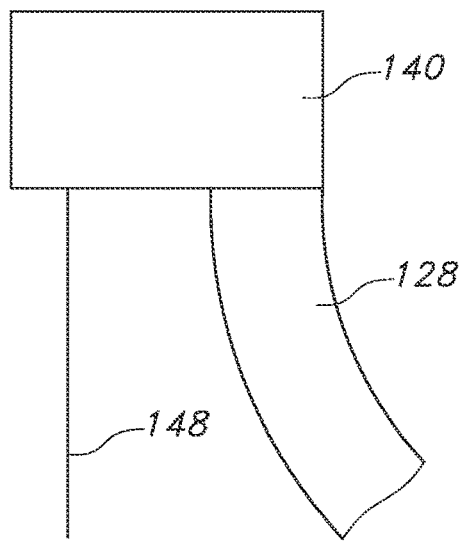
FIGS. 8 and 9 depict embodiments of the slidable connection of FIG. 7.

The sheath coupling 140, however, is not limited to the use of the outer sheath 104 for controlling its movement. As depicted in FIG. 8, the sheath coupling 140 may include a rod 148 secured thereto. The proximal end (not shown) of the rod 148 may be accessible at the proximal handle assembly 109. The rod 148 may be pulled or pushed at the proximal handle assembly 109 to control proximal or distal movement, respectively, of the sheath coupling 140. The rod 148 may be used in conjunction sheath coupling buttress embodiment of FIG. 9 or may be used without the sheath coupling buttress embodiment of FIG. 9.

Figure 10:
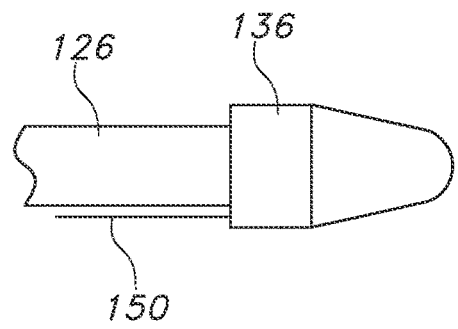
FIGS. 10 and 11 depict an embodiment for recapture of a nosecone of the internal iliac portion of the delivery system.
Figure 11:
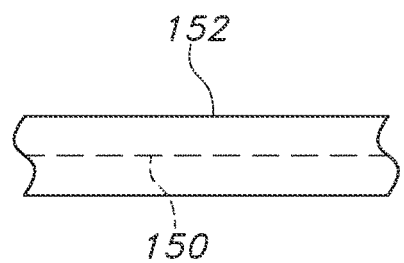

As described below, the integrated hypogastric delivery system 111 is returned within the outer sheath 104 after deployment of the hypogastric stent-graft. As depicted in FIGS. 10 and 11, the second nosecone 136 of the integrated hypogastric delivery system 111 may include a thread 150 attached to or associated with the second nosecone 136. The thread 150 may be disposed within a thread lumen 152. The thread 150 and/or thread lumen 152 may be disposed along the cannulate wire lumen 126, such as along the outside of the cannulate wire lumen 126 and underneath the stent-graft disposed over the cannulate wire lumen 126. A proximal portion (not shown) of the thread 150 may be accessible at the proximal handle assembly 109. The thread 150 may be pulled proximally at the proximal handle assembly 109 to facilitate, if necessary, the re-sheathing of the integrated hypogastric delivery system 111, including the second nosecone 136, within the outer sheath 104.

The present invention, however, is not limited to the use of the thread 150 to aid in the re-sheathing of the integrated hypogastric delivery system 111. Other techniques and devices, as depicted in FIGS. 12 and 13, may be used in conjunction with or without thread 150.

As depicted in FIG. 12, for example, a slidable snare 142 may be used to aid in the re-sheathing of the integrated hypogastric delivery system 111. The slidable snare 142 may be disposed over the second outer sheath 128, and when the proximal portion of the slidable snare 142 (not shown) is pulled proximally at the proximal handle assembly 109, the integrated hypogastric delivery system 111 is moved towards an abutting or adjacent relationship with respect the main guidewire 118 or guidewire lumen 120 to facilitate re-sheathing within the outer lumen 104.

As depicted in FIG. 13, for example, a slidable sleeve 144 may be disposed over the second outer sheath 128. A pull wire 146 for slidable sleeve 144 may be pulled proximally at the proximal handle assembly 109 to slide the sleeve 144 proximally over the second outer sheath 128, whereby the integrated hypogastric delivery system 111 is moved towards an abutting or adjacent relationship with respect to the main guidewire 118 or guidewire lumen 120 to facilitate re-sheathing within the outer lumen 104.

FIGS. 14-20 depict various deployment stages of the delivery system of catheter 100 having the integrated hypogastric delivery system 111.

The deployment sequence and devices for achieving the same are further described in conjunction with FIGS. 6-11. The present invention is not limited to stages depicted in FIGS. 6-11, and modifications or variations of these stages may suitably be used.

For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. In some applications a delivery sheath may not be needed and the delivery catheter 100 of the present invention may be directly inserted into the patient's access vessel by either arteriotomy or percutaneous puncture.

Figure 14:
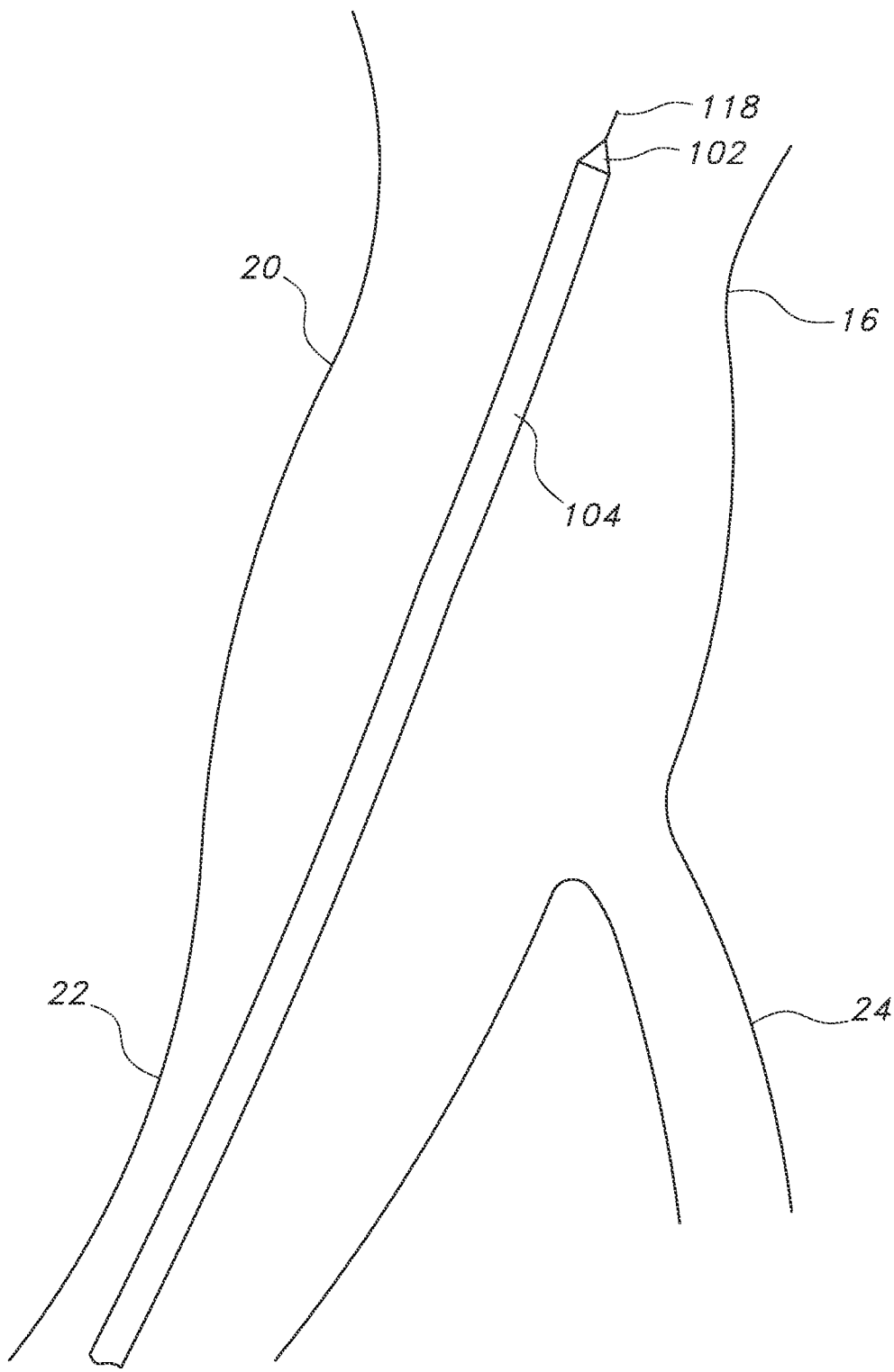
FIG. 14 depicts initial deployment of the delivery system or catheter of FIG. 2 via an external iliac artery and within an iliac aneurysm.

As depicted in FIG. 14, delivery system or catheter 100 is deployable via the external iliac artery 22 towards or beyond the iliac aneurysm 20 over the main guidewire 118. The outer sheath 104 is in its initial deployment stage, such as depicted in FIG. 2. The nosecone 102 or distal portion of the delivery system or catheter 100 is positioned beyond the hypogastric artery 24.

Figure 15:
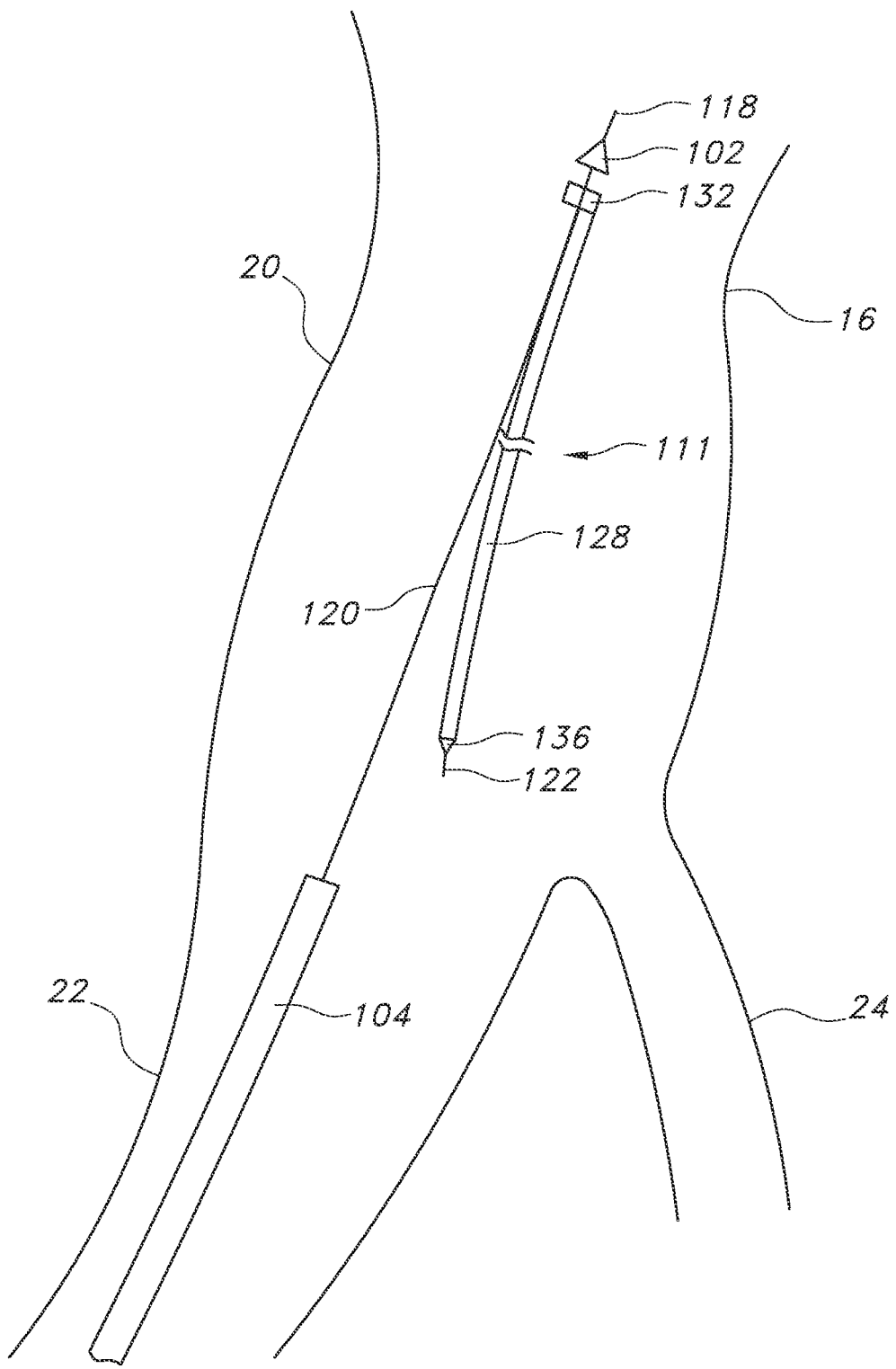
FIG. 15 depicts an unsheathed delivery system or catheter of FIG. 14.
Figure 16:
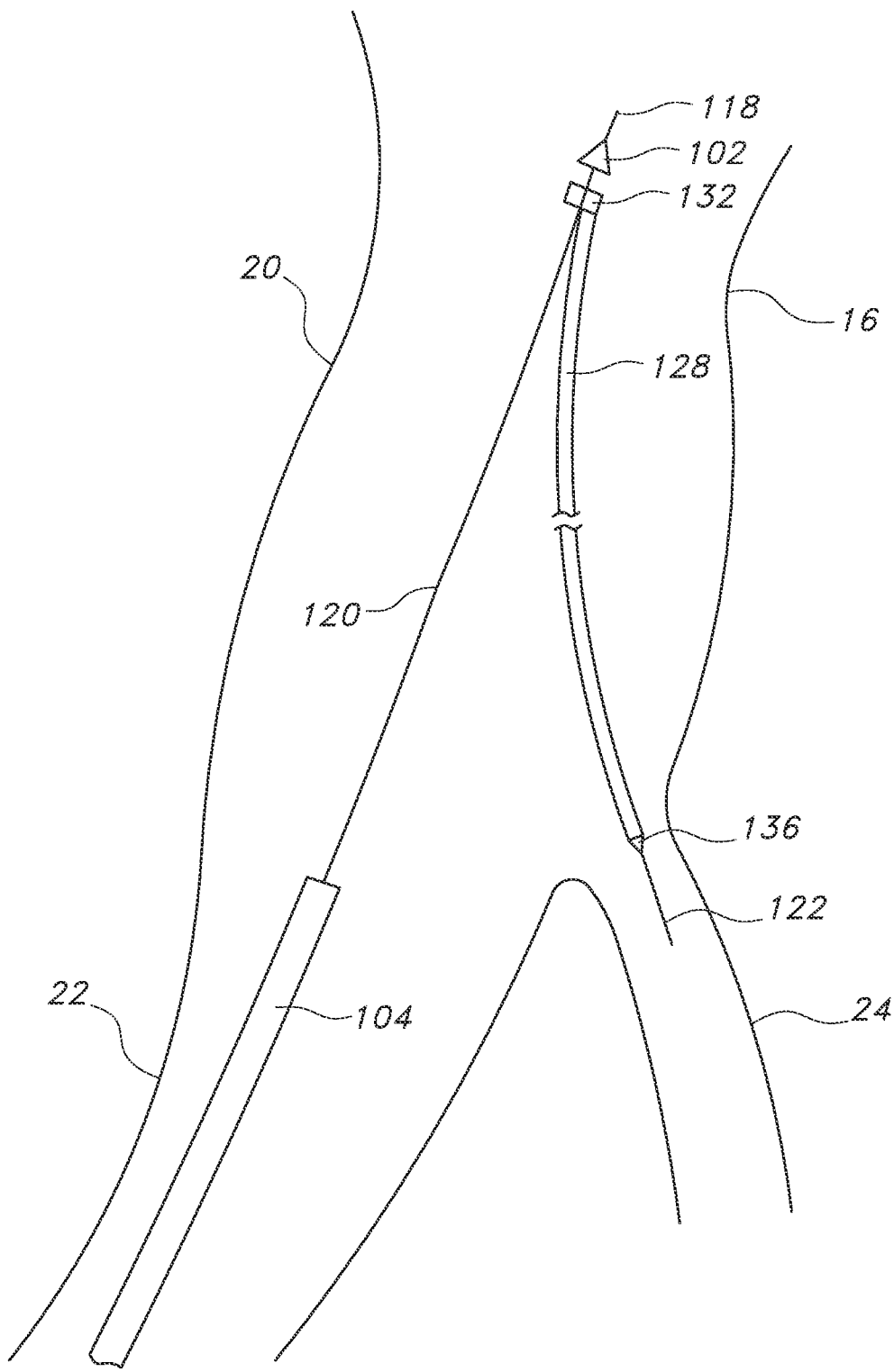
FIG. 16 depicts cannulation of a hypogastric artery with the delivery system or catheter of FIG. 14.

As depicted in FIG. 15, the outer sheath 104 is withdrawn or pulled proximally to unsheathe the integrated hypogastric delivery system 111. As depicted in FIG. 16, the iliac artery 16 is then cannulated with the hypogastric cannulate wire 122. In FIGS. 15 and 16 the slidable connection 132 is positioned distally to permit access of the hypogastric cannulate wire 122 into the hypogastric artery 24.

Figure 17:
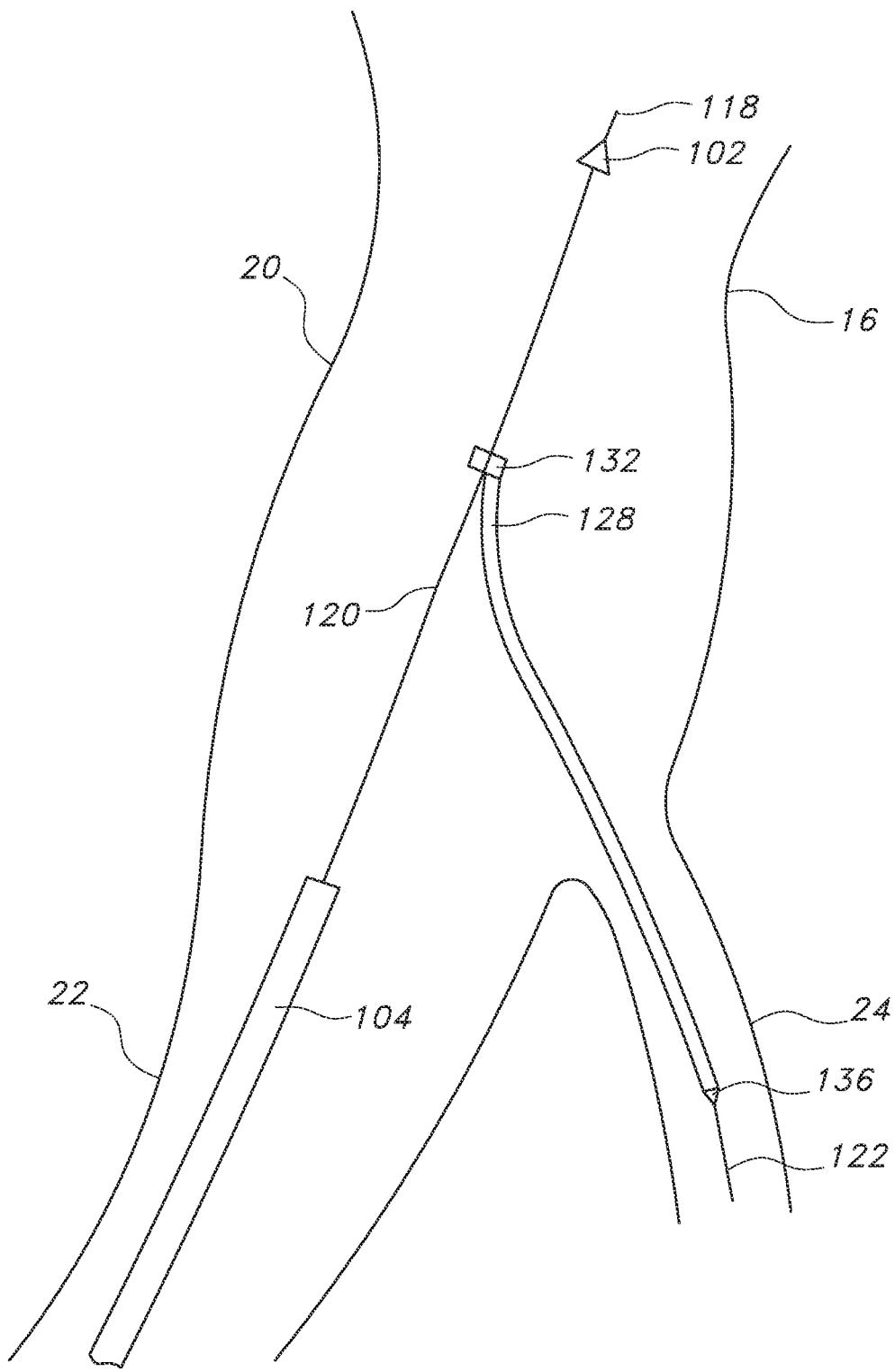
FIG. 17 depicts deployment of a portion of the delivery system or catheter of FIG. 14 within a hypogastric artery.
Figure 18:
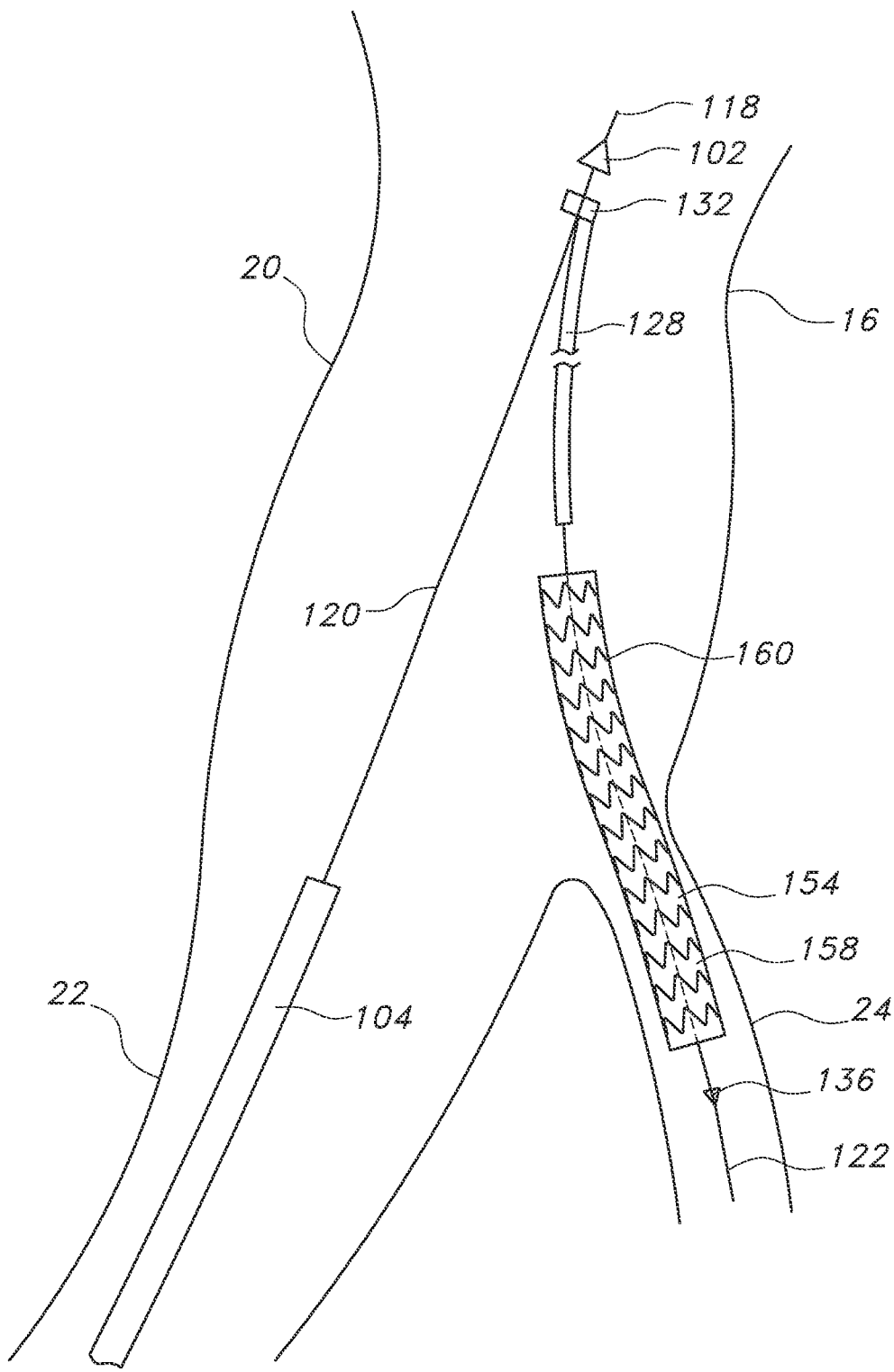
FIG. 18 depicts deployment of a stent-graft within a portion of the hypogastric and iliac arteries.

In FIG. 17, the slidable connection 132 is retracted proximally to advance the proximal portion of the second outer sheath 128 into the hypogastric artery 24. In FIG. 18, the second outer sheath 128 is withdrawn or retracted distally to uncover the hypogastric stent-graft 154. In one embodiment, the expandable stent-graft 154 is a non-fenestrated stent-graft having no open passageways extending through a wall of the expandable stent-graft. As used herein, the term non-fenestrated refers to a lack of discrete openings or passageways in the wall of a stent-graft through which may provide, for example, access for auxiliary delivery components, such as but not limited to delivery catheters and guidewires. Such openings or passageways, however, exclude porosity, if any, in the wall of the graft itself. The distal portion of the hypogastric stent-graft 154 is deployed within the hypogastric artery 24. Upon deployment or expansion of the hypogastric stent-graft 154, the distal portion 158 of stent-graft 154 may sealingly engage the lumen of the hypogastric artery 24. The proximal portion 160 of stent-graft 154 is typically disposed within the iliac aneurysm 20, but, if desired, may be disposed within the iliac artery 16.

Figure 19:
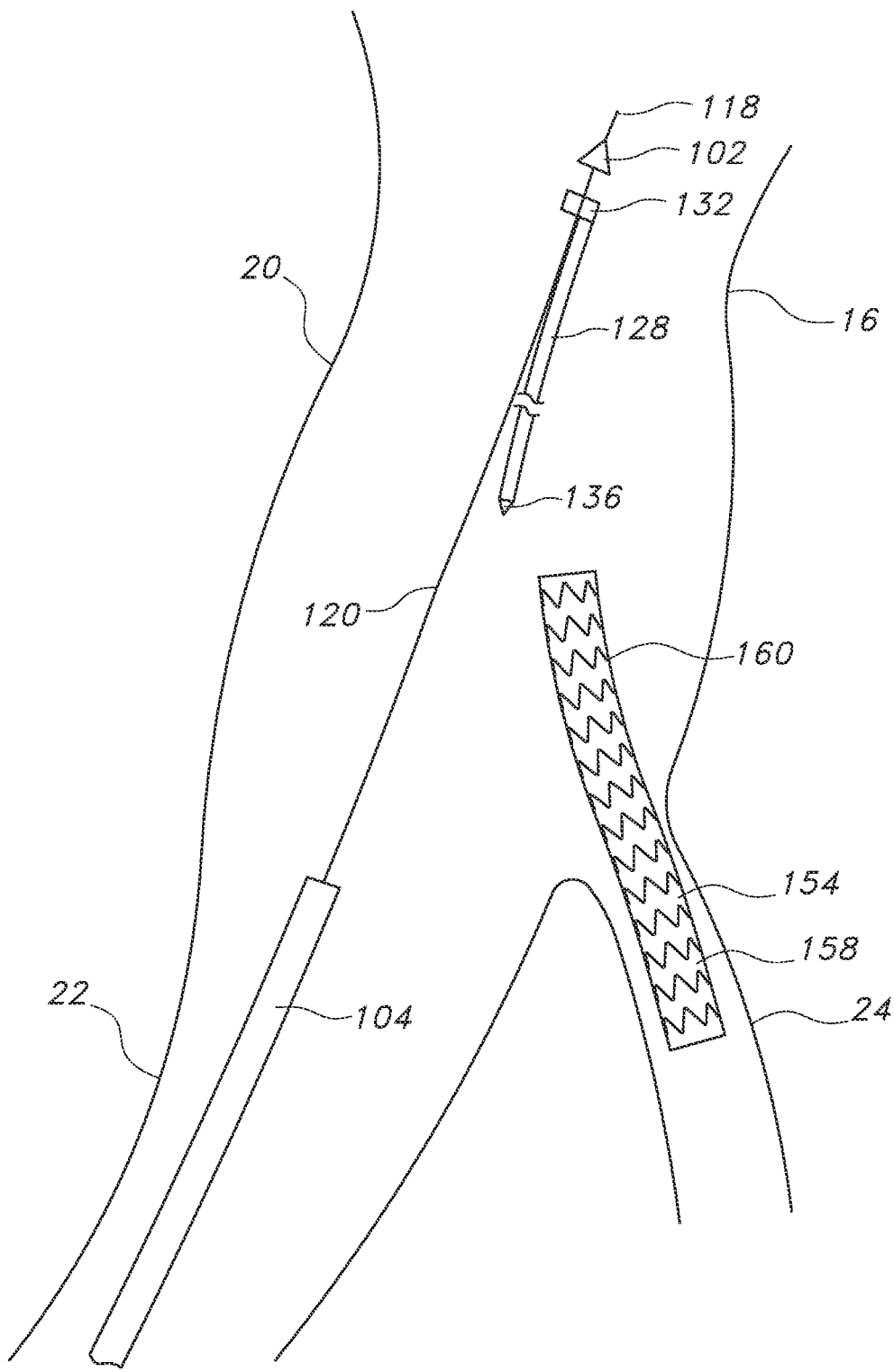
FIGS. 19 and 20 depict withdrawal stages of the delivery system or catheter of FIG. 2.

In FIG. 19, the hypogastric cannulate wire 122 is retracted within the second outer sheath 128. The second outer sheath 128 is moved proximally adjacent or otherwise near, for example, moving the proximal portion of the second outer sheath 128, the main guidewire lumen 120. The second nosecone 136 is recaptured, either partially or in total, within the second outer sheath 128.

Figure 20:
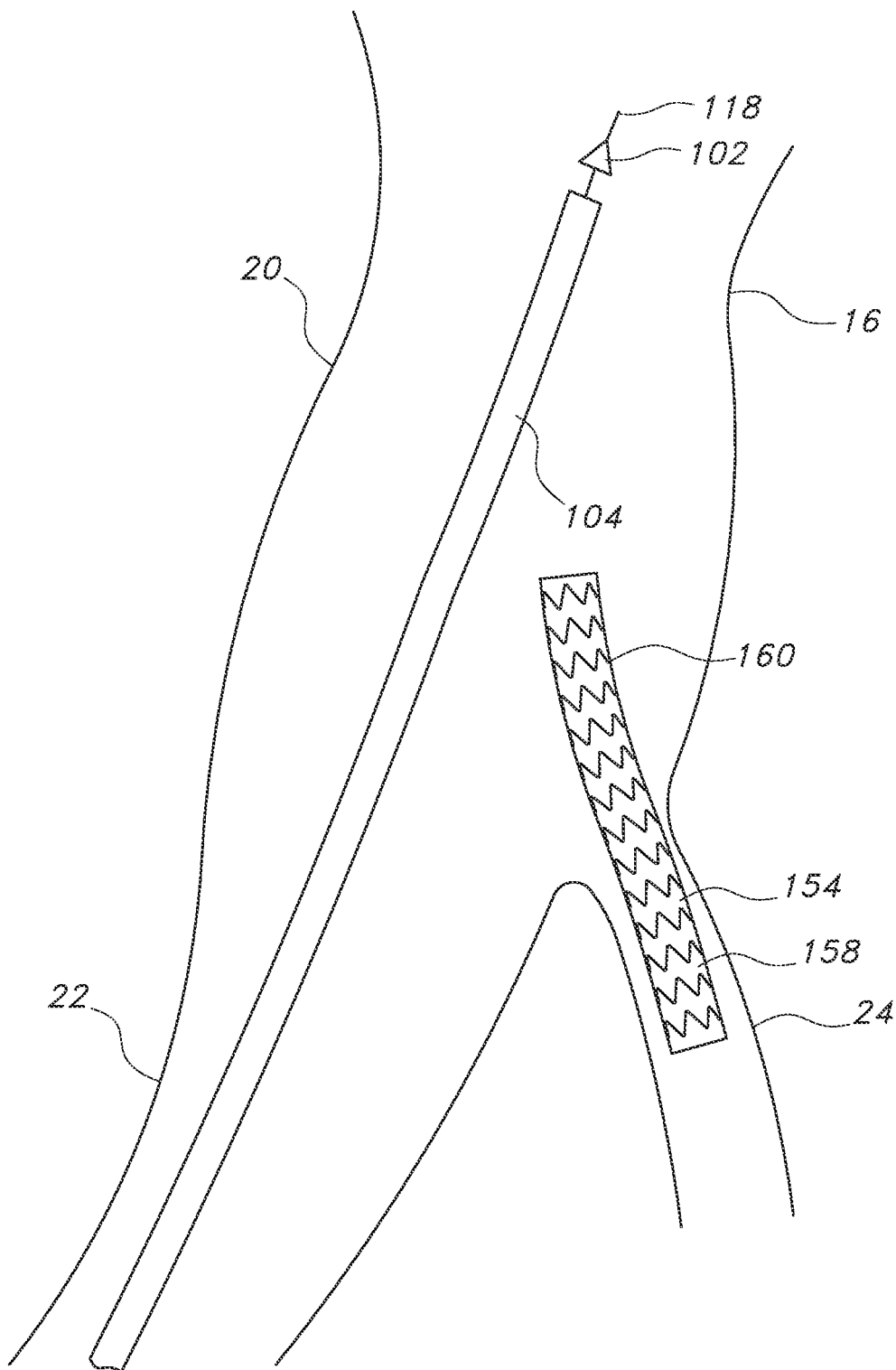

In FIG. 20, the outer sheath 104 is advanced distally to re-sheathe the integrated hypogastric delivery system 111.

Figure 21:
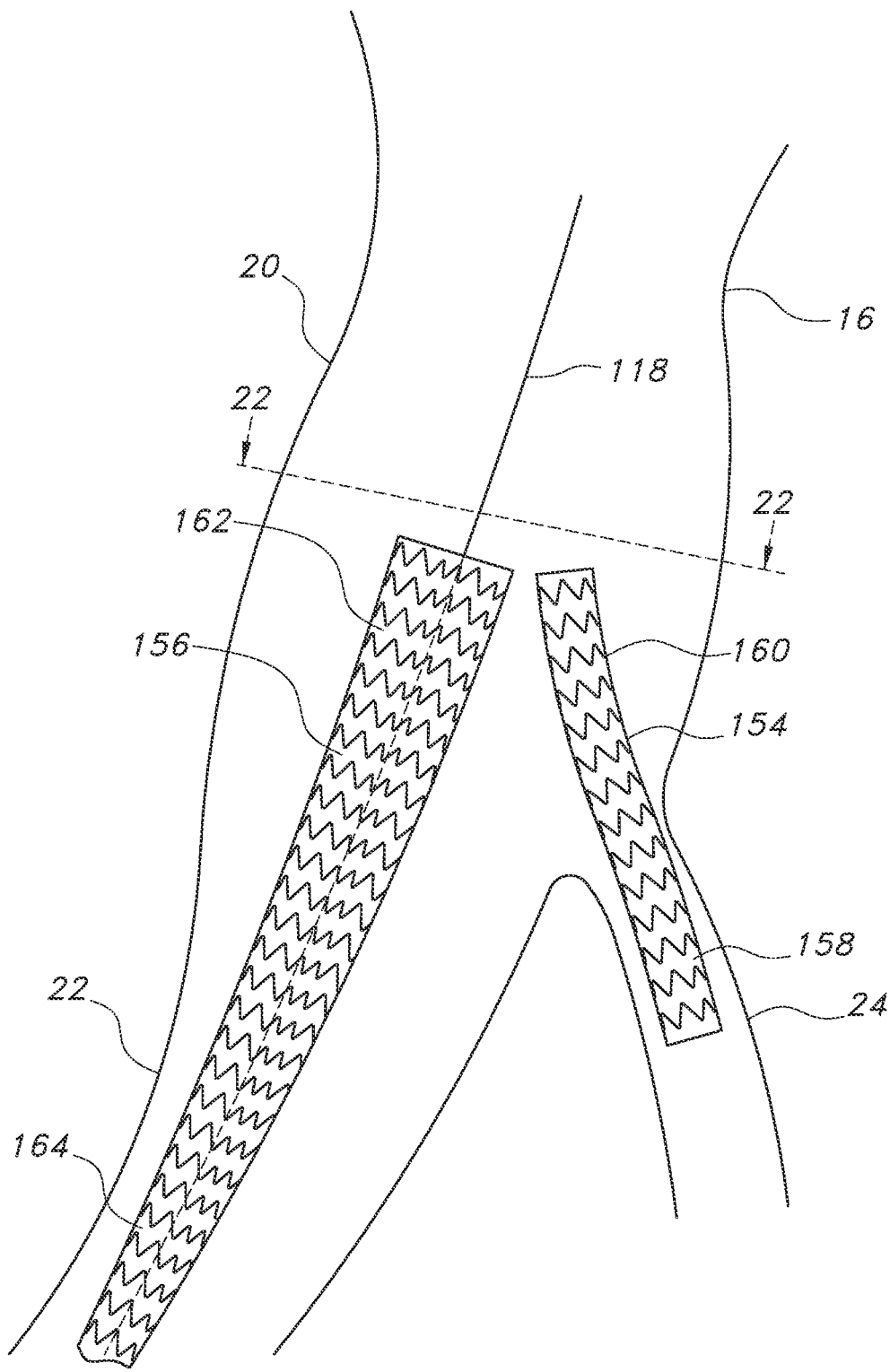
FIG. 21 depicts stent-grafts deployed within a portion of the hypogastric and external iliac arties and a portion of an iliac aneurysm.

In FIG. 21 an iliac stent-graft 156 is deployed, typically with another catheter (not shown) over the main guidewire 118. The proximal portion 162 of stent-graft 156 is typically disposed within the iliac aneurysm 20, but, if desired, may be disposed within the iliac artery 16. The proximal end of the proximal portion 160 of stent-graft 154 and the proximal end of the proximal portion 162 of stent-graft 156 are positioned to be in substantial side-by-side relationship, but some overlap is acceptable. The distal portion 164 of stent-graft 156 is deployed in the external iliac artery 22.

Figure 22:
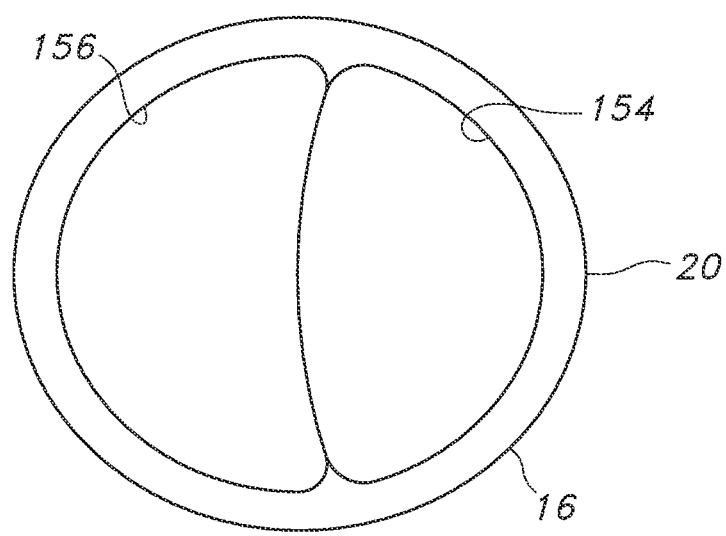
FIG. 22 is a cross-section view of the deployed stent-grafts of FIG. 21.
Figure 23:
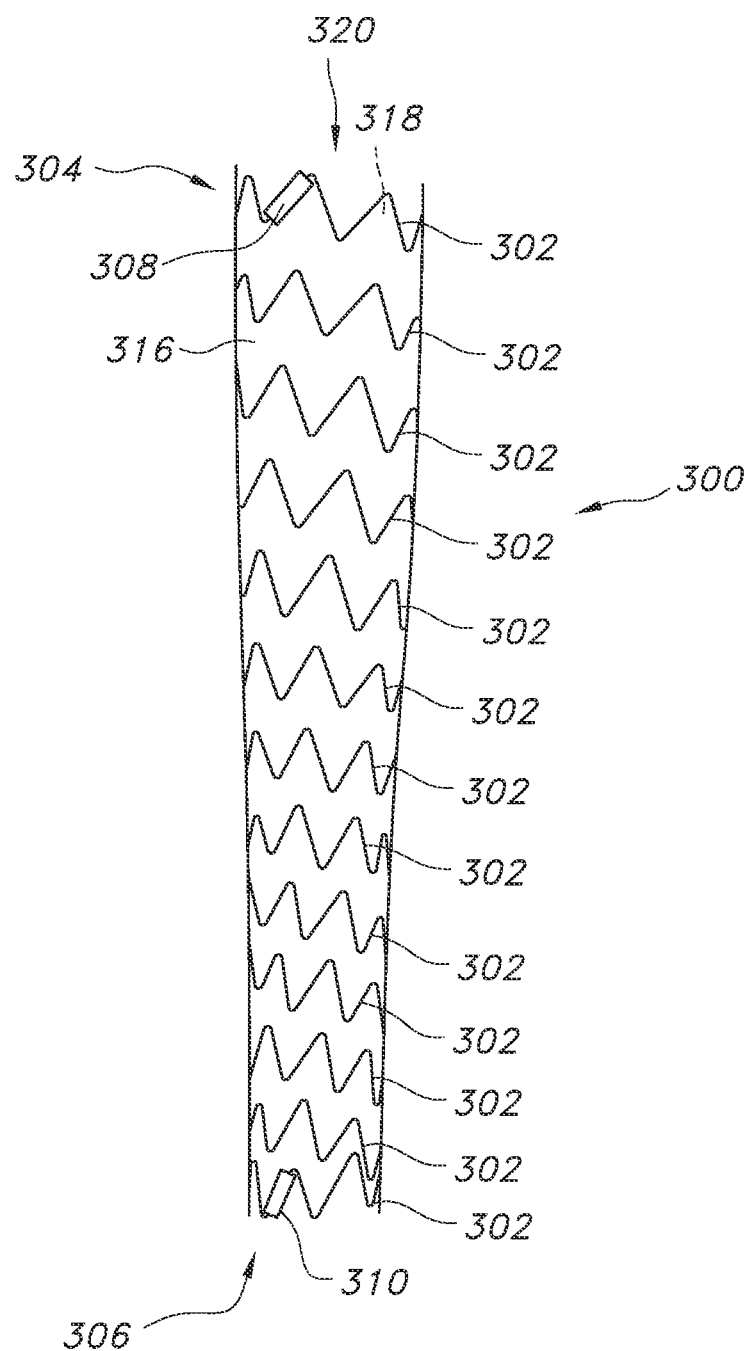
FIGS. 23, 24 and 25 depict various embodiments of stent structures useful in the present invention.

FIG. 22 is a cross-section view of the hypogastric stent-graft 154 and the iliac stent-graft 156 within the iliac artery 16 or iliac aneurysm 20. The hypogastric stent-graft 154 and the iliac stent-graft 156 are conformable as to provide a substantial seal within the iliac artery 16 or iliac aneurysm 20 or even within another stent-graft as described below, thus preserving proper blood flow.

Graft portions of the stent-grafts 154, 156 may include wall portions made from any biocompatible, durable material, including, for example polyethylene; polypropylene; polyvinyl chloride; polytetrafluoroethylene (PTFE); fluorinated ethylene propylene; fluorinated ethylene propylene; polyvinyl acetate; polystyrene; poly(ethylene terephthalate); naphthalene dicarboxylate derivatives, such as polyethylene naphthalate, polybutylene naphthalate, polytrimethylene naphthalate and trimethylenediol naphthalate; polyurethane, polyurea; silicone rubbers; polyamides; polyimides; polycarbonates; polyaldehydes; polyether ether ketone; natural rubbers; polyester copolymers; silicone; styrene-butadiene copolymers; polyethers; such as fully or partially halogenated polyethers; and copolymers and combinations thereof. Desirably, the graft materials are non-textile graft materials, e.g., materials that are not woven, knitted, filament-spun, etc. that may be used with textile grafts. Such useful graft material may be extruded materials. Particularly useful materials include porous polytetrafluoroethylene without discernible node and fibril microstructure and (wet) stretched PTFE layer having low or substantially no fluid permeability that includes a closed cell microstructure having high density regions whose grain boundaries are directly interconnected to grain boundaries of adjacent high density regions and having substantially no node and fibril microstructure, and porous PTFE having no or substantially no fluid permeability. PTFE layers lacking distinct, parallel fibrils that interconnect adjacent nodes of ePTFE and have no discernible node and fibril microstructure when viewed at a scanning electron microscope (SEM) magnification of 20,000. A porous PTFE layer having no or substantially no fluid permeability may have a Gurley Number of greater than about 12 hours, or up to a Gurley Number that is essentially infinite, or too high to measure, indicating no measurable fluid permeability. Some PTFE layers having substantially no fluid permeability may have a Gurley Number at 100 cc of air of greater than about $10^6$ seconds. The Gurley Seconds is determined by measuring the time necessary for a given volume of air, typically, 25 cc, 100 cc or 300 cc, to flow through a standard 1 square inch of material or film under a standard pressure, such as 12.4 cm column of water. Such testing maybe carried out with a Gurley Densometer, made by Gurley Precision Instruments, Troy, New York. Details of such useful PTFE materials and methods for manufacture of the same may be found in commonly owned U.S. Pat. No. 8,728,372 to Humphrey et al, entitled "PTFE Layers and Methods of Manufacturing", which is incorporated by reference in its entirety herein.

The graft portions may be formed from an inner layer or layers and outer layer or layers of flexible graft material, such as PTFE or ePTFE. In one embodiment, the flexible graft material includes PTFE which is substantially porous but includes no discernible node and fibril structure. The inner and outer layers of graft material may be formed from tubular extrusions, laminated wraps of multiple layers of graft material or materials, and the like. The inner or outer layers of graft material may be permeable, semi-permeable or substantially non-permeable for some embodiments.

The stent-grafts 154, 156 are desirably stent-graft devices. A first radially expandable stent 300 may be interposed between an outer layer (not shown) and inner layer (not shown) of graft material for these legs. The interposed stent disposed between the outer layer and inner layer of graft material may be formed from an elongate resilient element helically wound with a plurality of longitudinally spaced turns into an open tubular configuration. The helically wound stent may be configured to be a self-expanding stent or radially expandable in an inelastic manner actuated by an outward radial force from a device such as an expandable balloon or the like. Some tubular prosthesis embodiments that may be used for graft extensions 118 and 120 are discussed in U.S. Pat. No. 6,673,103 to Golds et al., entitled "Mesh and Stent for Increased Flexibility", which is hereby incorporated by reference in its entirety herein.

The stent or wire portions of the stent-grafts 154, 156 may be made from stainless steel, nickel titanium alloy (NiTi), such as NITINOL, or any other suitable material, including, but not limited to, cobalt-based alloy such as ELGILOY, platinum, gold, titanium, tantalum, niobium and combinations thereof. The stent-grafts 154, 156 may be balloon-expandable or self-expandable. If stent-graft 154 is balloon-expandable, then the integrated hypogastric delivery system 111 may include a balloon (not shown) disposed over the cannulate wire lumen 126 to expand such a stent-graft. The balloon may be inflated and deflated through a balloon fluid port and lumen (not shown) in the delivery system. In such a case the second outer sheath 128 may be eliminated from the integrated hypogastric delivery system 111.

As shown in more detail in FIGS. 23, 24, 25, 26A-26E, 27A, 27B and 28, a generally tubular stent 300 may be provided for the stent-grafts 154, 156. The tubular stent 300 includes a helically-wound, undulating wire forming a series of adjacent helical windings 302, which may be made from the materials described above (including a resilient metal such as nitinol). The ends 304, 306 of the stent 300 may be secured to adjacent ring portions of the stent at distinct areas. For example, a first end may be adjoined via a first securement point 308, and a second end may be joined at a second securement point 310, as shown to avoid exposure of element ends to either PTFE graft material or possible patient tissues. In a preferred embodiment, the securement points 308, 310 are located proximal to the first end 304 and second end 306, respectively, with no other securement points on the stent 300. That is, aside from the helical windings 302 at the first end 304 (which may be referred to as a proximal end 304) and second end 306 (which may be referred to as a distal end 306), respectively, adjacent approximate circumferential windings 302 in the stent 300 may be free of interconnecting securement points. Any securement means may be used, including, for example, welding, such as struts and welds. It is desired that the relative stiffness of a stent be greater than the stiffness of the PTFE graft material so as to provide beneficial kink resistance.

The undulating wire may be a continuous element forming a series of helical windings 302 extending from one end 304 of the extension to the other end 306 thereof. The tubular stent 300 thus has an internal lumen 320 extending there through, from the first end 304 to the second end 306. The ends 304, 306 of the elongate element may be secured to adjacent ring members by any suitable means such as adhesive bonding, welding such as laser welding, soldering or the like. For some embodiments, the stent element may have a transverse dimension or diameter of about 0.005 inch to about 0.015 inch. As may be seen in FIGS. 24 and 25, the stent 300 may be tapered or flared. In addition, if desired, adjacent helical windings 302 may be in an arrangement 315 such that adjacent helical windings 302 at one end (either the first end 304 or second end 306) have an acute angle formation at a portion of the stent 300 proximal to the end of the stent 300. That is, if desired, the helical winding closest to the end (shown as 302') may have an approximately 180° angle with respect to the longitudinal axis, while the helical winding next to this helical winding (shown as 302") has an angle less than 180°. These two helical windings (302' and 302") may be attached at securement points 308, 310.

Figures 26A, 26B:
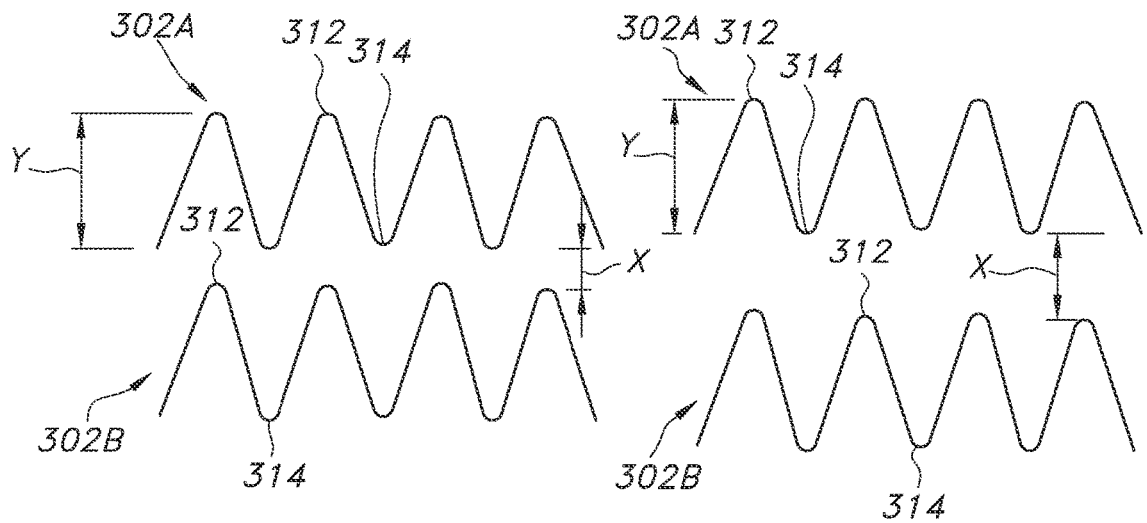
FIGS. 26A through 26E depict various arrangements of helically wound stents of the present invention.
Figures 26C, 26D:
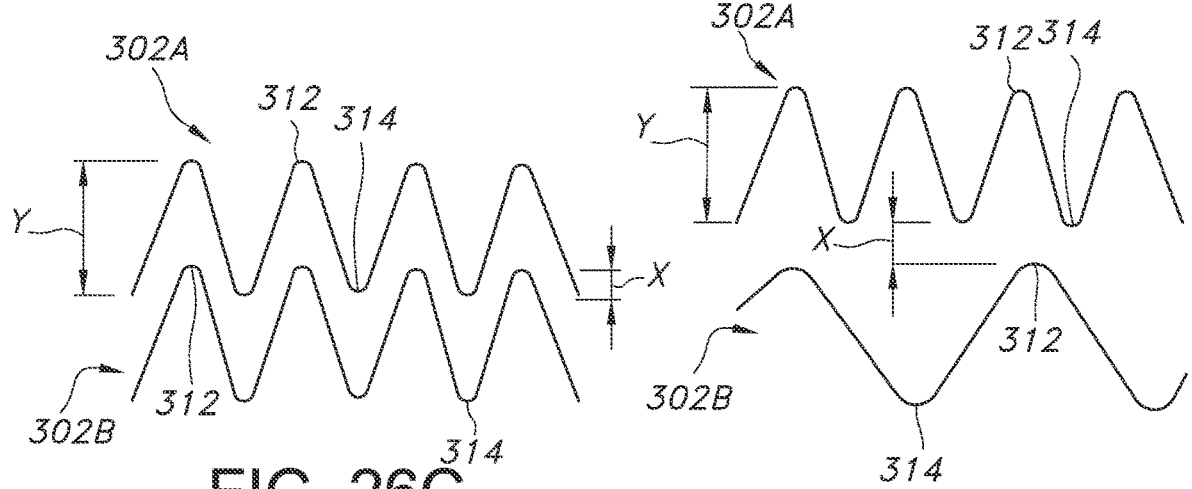
Figure 26E:
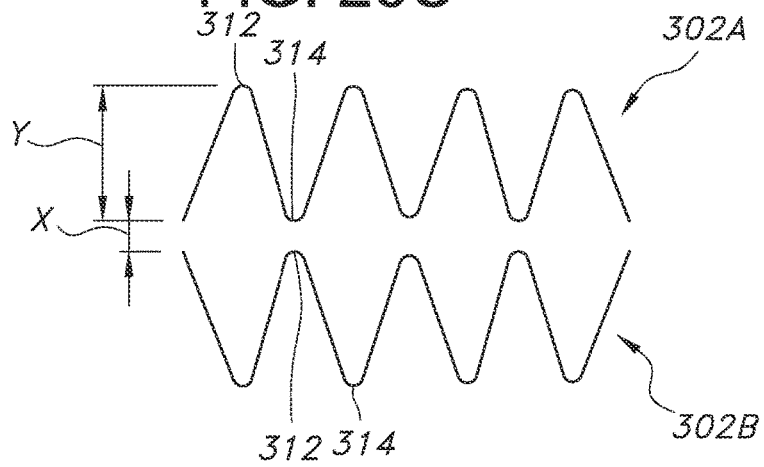
Figure 27A:
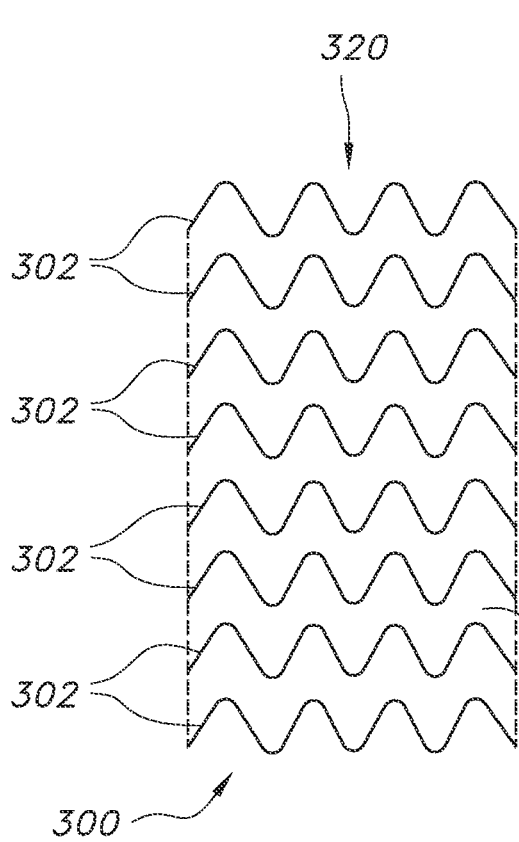
FIGS. 27A and 27B depict stent-graft assemblies useful in the present invention.
Figure 27B:
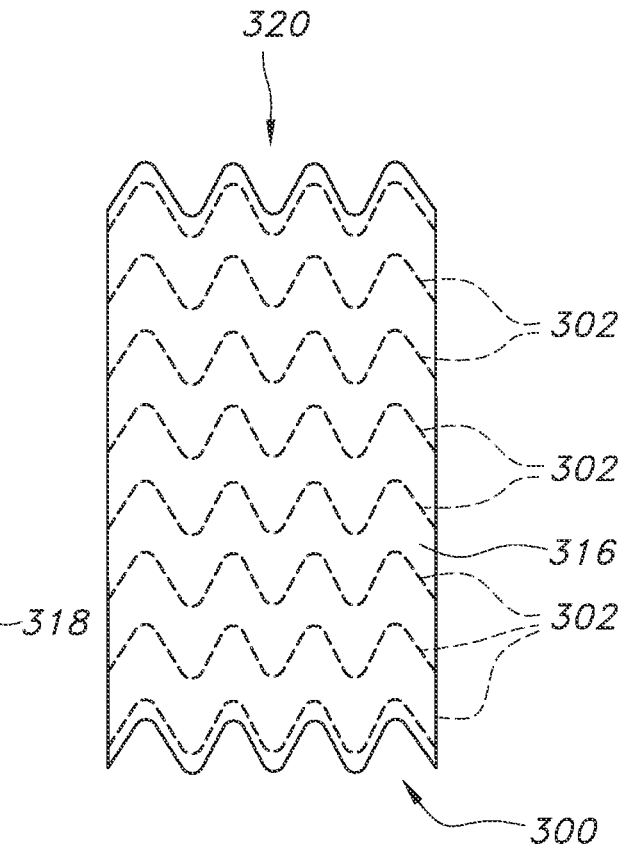
Figure 28:
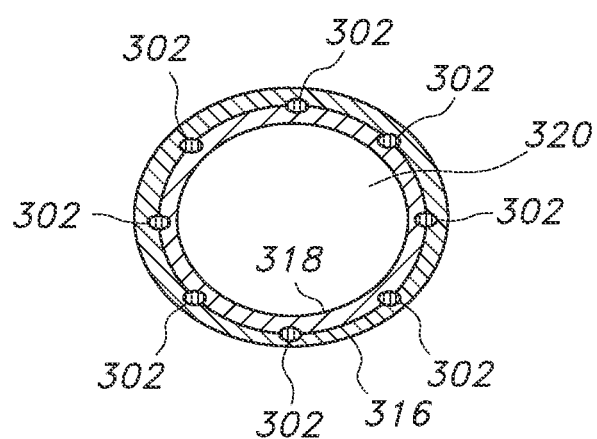
FIG. 28 is a top cross sectional view of one embodiment of a stent-graft assembly of the present invention.

FIGS. 26A through 26E depicts various arrangements of the helical windings 302 formed by the undulating wire in forming the stent 300. Adjacent helical windings are depicted as 302A and 302B, but it will be understood that the arrangement depicted in FIGS. 26A through 26E may be applied to each helical winding 302 in the stent 300. Alternatively, the arrangements depicted in FIGS. 26A through 26E may be applied to only some of the helical windings 302 in the stent 300. Undulating wire of the stent 300 includes a series of peaks 312 and valleys 314 as the wire is helically wound. The arrangement of peaks 312 and valleys 314 may vary and may be arranged in any fashion desired. In some embodiments, such as that of FIG. 26A, the peaks 312 of one circumferential winding 302A may be substantially aligned with the peaks 312 of an adjacent circumferential winding 302B. As can be seen in FIG. 26B, the adjacent circumferential windings 302A and 302B may be spaced apart. As can be seen in FIG. 26C, the adjacent circumferential windings 302A and 302B may be closer together. In another embodiment, set forth in FIG. 26D, one peak 312 of one circumferential winding 302B may span two peaks 312 of an adjacent winding 302A. In another embodiment set forth in FIG. 26E, the peaks 312 of one circumferential winding 302A may be substantially aligned with the valleys 314 of an adjacent circumferential winding 302B. Other arrangements for the helical windings 302 are contemplated and will be readily understood by those of skill in the art.

The distances between adjacent windings 302A, 302B may vary along the length of the stent 300, where the distance at one end 304 is different than the distance at the second end 306. In each embodiment, there are two distances that should be considered. The first distance X is the distance between the lowest valley (314) of the first winding (302A) and the highest peak (312) of the second winding (302B). The second distance Y is the distance between the highest peak (312) and lowest valley (314) of the first winding (302A).

There may be at least two or more different ratios of X/Y (or equivalently X/Y) present in the device. The first ratio is where X/Y is a relatively large positive number, that is; there is a relatively larger separation between the distance (X) as compared to the distance (Y). The second ratio is where X/Y is a relatively smaller positive number, that is, there is a relatively smaller separation between the distance (X) as compared to the distance (Y). Finally, the third ratio is where X/Y is a negative number, that is, the lowest peak of the first winding (302A) dips to a point lower than the highest peak of the second winding (302B).

The ratio X/Y can be manipulated to obtain the desired properties of the stent-graft in a local region. A relatively large X/Y ratio (preferably greater than about 0.5) produces a highly flexible region of a stent-graft. A smaller X/Y ratio (preferably from about 0.1 to about 0.5) produces regions of a stent-graft with moderate flexibility and moderate radial force. A region of a stent-graft with an even smaller or negative X/Y ratio (preferably less than about 0.1) has a relatively high radial force with relatively less flexibility. The ranges for X/Y described above are appropriate when the stent height Y is from about one-third of the diameter D of the stent to about equal to the diameter D of the stent. If Y is larger than this when compared to D, then the ranges for the X/Y ratios described above will be reduced. Similarly, if Y is much smaller than the stent diameter D, then the numerical values for the ranges above will be increased.

Using the principle described above, a stent-graft can be constructed with varying ratios of X/Y along the length to achieve desired properties. For example, if a stent-graft is used as an iliac limb in a modular endovascular graft for abdominal aortic aneurysms (AAAs), it may be desirable for the proximal end of the stent-graft to have a relatively high radial force to maximize anchorage into the aortic body component of the modular system. In this case, the proximal end of the iliac limb could be designed with a small or negative X/Y ratio, such as −0.5, and Y may be chosen to be, for example, from about one fifth to one half of the stent-graft diameter. In this region flexibility is less important than radial force so the negative X/Y ratio yields the desired properties. In the middle of the stent-graft flexibility becomes important to accommodate the tortuous common iliac arteries often found in AAA patients. It may then be desirable to have a relatively large X/Y ratio, such as about 0.55, to achieve this flexibility. Near the distal end of the stent-graft it may again be desirable to have more radial force to promote anchorage and sealing of the iliac limb into the common iliac artery of the patient, but not as much radial force as at the proximal end. In this case, it may be desirable to have an X/Y ratio near zero, or from about −0.1 to about 0.3.

Since the stent is formed in a helix along the length of the stent-graft, it is possible to continuously vary the X/Y ratio to achieve the desired properties in various regions of the stent-graft with smooth variations and no abrupt changes along the length. These smooth variations promote conformance to the vasculature and avoid the stress and/or strain concentrations and potential kinking that can result from abrupt transitions in mechanical properties along the length of a stent-graft.

Figure 24:
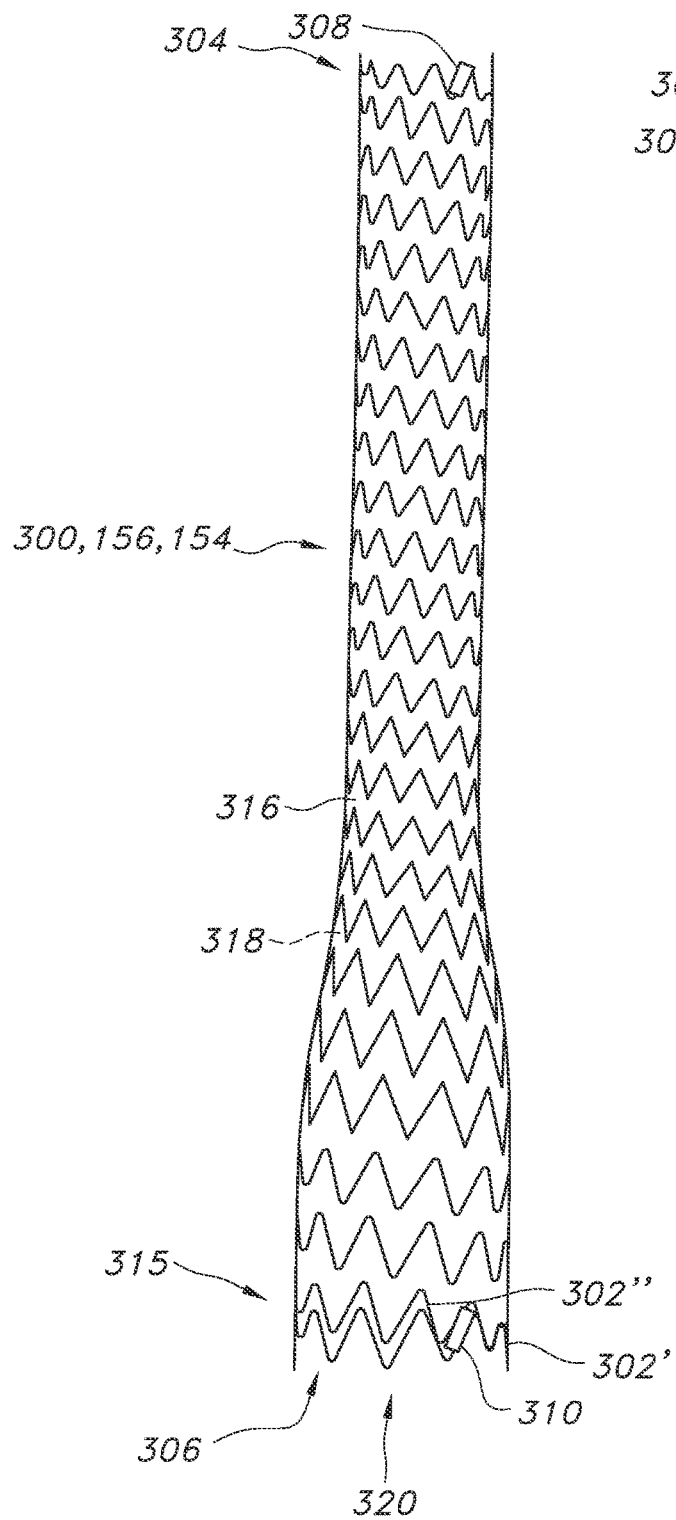
Figure 25:
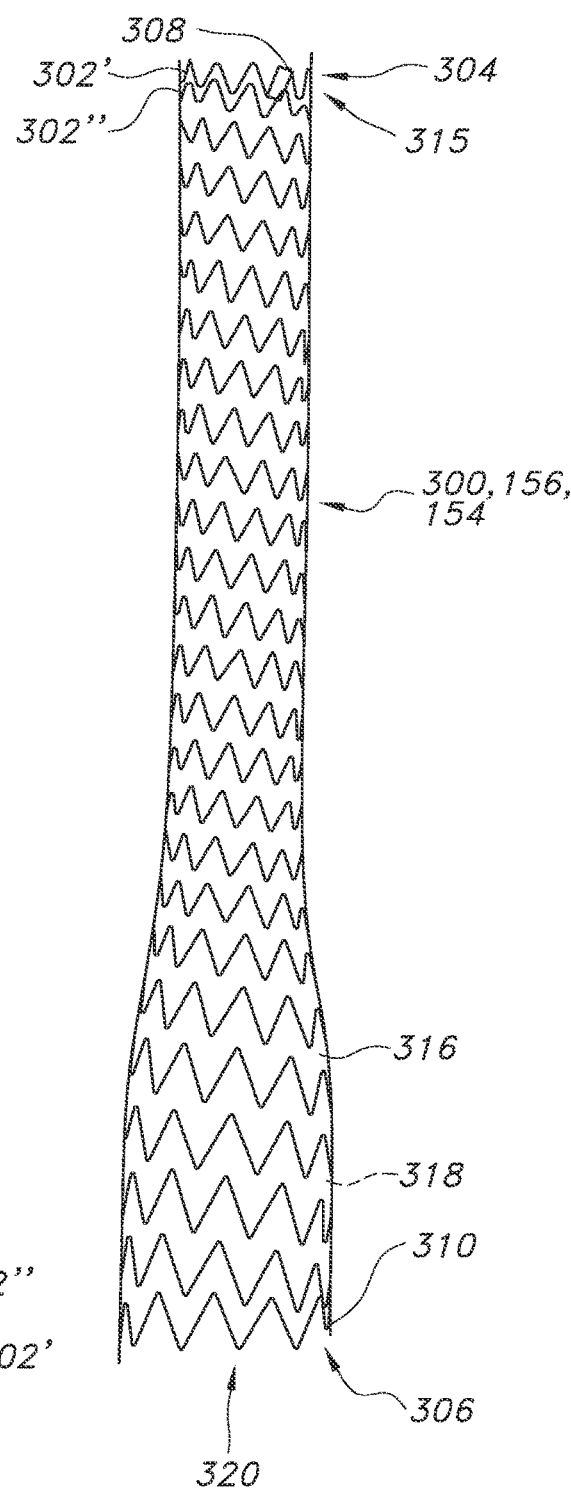

The stent 300 may include a longitudinal axis (generally defined along internal lumen 320) and a radial axis perpendicular to the longitudinal axis; where the helical windings 302 are wound at an acute winding angle of about 3 degrees to about 15 degrees with respect to the radial axis. As can be seen in FIGS. 24 and 25, the acute winding angle at a portion of the stent 300 proximal to the first end 304 is different from the acute winding angle at a portion of the stent 300 proximal to the second end 306. In some embodiments, a first helical winding 302 at the first end 304 may be perpendicular to the longitudinal axis. Further, it may be desired that a helical winding 302 at the second end 306 is perpendicular to the longitudinal axis. Helical windings 302 at the first end 304 and the second end 306 may both be perpendicular to the longitudinal axis, or only one may be perpendicular to the longitudinal axis. An adjacent peak 312 and an adjacent valley 314 of a helical winding 302 have a peak height from an apex of said adjacent peak to a base of said adjacent valley. It may be desired that the peak height at a portion of the stent 300 proximal to the first end 304 of the stent 300 is different from the peak height at a portion of the stent 300 proximal to the second end 306 of the stent 300.

At least one graft layer may be disposed on the stent 300. The placement of the graft layers may best be seen in FIGS. 27A, 27B and 28. In some embodiments, an inner graft layer 318 may be disposed on the interior surface of the helically wound stent 300, forming inner lumen 320. A second graft layer 316 may be disposed on the outer surface of the helically wound stent 300, forming an outside surface. More than one or two layers of graft material may be disposed on the interior or exterior of the helically wound stent 300 as desired. For some embodiments of the first and/or second stent-grafts 80, 90, layers of materials having different properties may be used in combination to achieve a desired clinical performance. For example, some layers of PTFE covering the stent 300 may be permeable, semi-permeable or substantially non-permeable depending on the desired performance and material properties. The layers 316 and 318 may be applied by a variety of methods and have a variety of configurations. For example, some layer embodiments may include extruded tubular structures applied axially over a mandrel or subassembly. Some layer embodiments graft layers 316 and 318 may be applied by wrapping layers circumferentially or wrapping tapes or ribbons in an overlapping helical pattern. For some embodiments, the outer layer 316 may be made from or include a semi-permeable or substantially non-permeable PTFE layer and the inner layer 318 may be made of or include a permeable layer of PTFE.

The first and/or second stent-grafts 154, 156 may be made by forming the layers of material 316, 318 together with the helically wound stent 300 over a mandrel, such as a cylindrical mandrel (not shown). Once the innermost layer 316 of the first or second stent-grafts 80, 90 has been wrapped about a shaped mandrel, a helical nitinol stent, such as helical stent 300, may be placed over the innermost layered PTFE layer 316 and underlying mandrel. If desired, one or more additional layers 318 of graft material may be wrapped or otherwise added over the exterior of the stent 300. If desired, the outer layer 318 may include low permeability PTFE film or PTFE film having substantially no permeability that does not have the traditional node fibril microstructure. The mandrel may then be covered with a flexible tube such that the layers 316, 318 and stent 300 are sandwiched under pressure and sintered so as to raise the temperature for the PTFE material to undergo a melt transformation in order to lock in its geometry and strength. The flexible tube (a manufacturing aid not shown) is removed from over the device and the resultant first and/or second stent-grafts 154, 156 are removed from the mandrel.

The graft portions of the first and/or second stent-grafts 154, 156 may be made at least partially from polytetrafluoroethylene (PTFE) which may include expanded polytetrafluoroethylene (ePTFE). In particular, main graft 10 and graft legs 118 and 120 may include any number of layers of PTFE and/or ePTFE, including from about 2 to about 15 layers, having an uncompressed layered thickness of about 0.003 inches to about 0.015 inches for the supple graft material or materials alone without supporting or ancillary structures such as high strength stents, connector rings or the like. Such graft body sections may also include any alternative high strength, supple biocompatible materials, such as DACRON, suitable for graft applications. Descriptions of various constructions of graft body sections as well as other components of graft assembly that may be used in any suitable combination for any of the embodiments discussed herein may be found in U.S. Pat. No. 7,125,464 to Chobotov et al., entitled "Method and Apparatus for Manufacturing an Endovascular Graft Section"; U.S. Pat. No. 7,090,693 to Chobotov et al., entitled "Endovascular Graft Joint and Method of Manufacture"; U.S. Pat. No. 7,147,661, entitled "Method and Apparatus for Shape Forming Endovascular Graft Material", to Chobotov et al.; U.S. Pat. No. 7,147,660 to by Chobotov et al., entitled "Advanced Endovascular Graft"; and U.S. Pat. No. 8,728,372 to Humphrey et al., entitled "PTFE Layers and Methods of Manufacturing"; the entirety of each of which is incorporated herein by reference.

Additional details of the above-described graft assemblies, including modular components, may be found in U.S. Patent Application Publication No. 2013/0261734 to Young et al., entitled "Advanced Kink Resistant Stent Graft"; the entirety of which is incorporated herein by reference.

Various methods of delivery systems and delivery of the device into a patient include those described in U.S. Patent Application Publication No. 2009/0099649 to Chobotov et al., entitled "Modular Vascular Graft for Low Profile Percutaneous Delivery", the contents of which are incorporated by reference in entirety herein. For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and a delivery catheter may be directly inserted into the patient's access vessel by either arteriotomy or percutaneous puncture.

The systems, devices, methods and techniques of the present invention may be used together with systems, devices, methods and techniques for treating abdominal aortic aneurysms. Details of the endovascular prosthesis and/or graft extensions useful for treating abdominal aortic aneurysms may be found in commonly owned U.S. Pat. Nos. 6,395,019; 7,081,129; 7,147,660; 7,147,661; 7,150,758; 7,651,071; 7,766,954 and 8,167,927 and commonly owned U.S. Published Application No. 2009/0099649, the contents of all of which are incorporated herein by reference in their entirety. Details for the manufacture of such endovascular prostheses may be found in commonly owned U.S. Pat. Nos. 6,776,604; 7,090,693; 7,125,646; 7,147,455; 7,678,217 and 7,682,475, the contents of all of which are incorporated herein by reference in their entirety. Useful inflation materials for the inflatable grafts may be found in may be found in commonly owned U.S. Published Application No. 2005/0158272 and 2006/0222596, the contents of all of which are incorporated herein by reference in their entirety. Additional details of suitable endovascular delivery systems for abdominal aortic aneurysms include, but are not limited to U.S. Patent Application Nos. 2013/0338752, 2013/0338753 and 2013/0338760, the contents of which are incorporated the herein by reference in their entirety.

Figure 29:
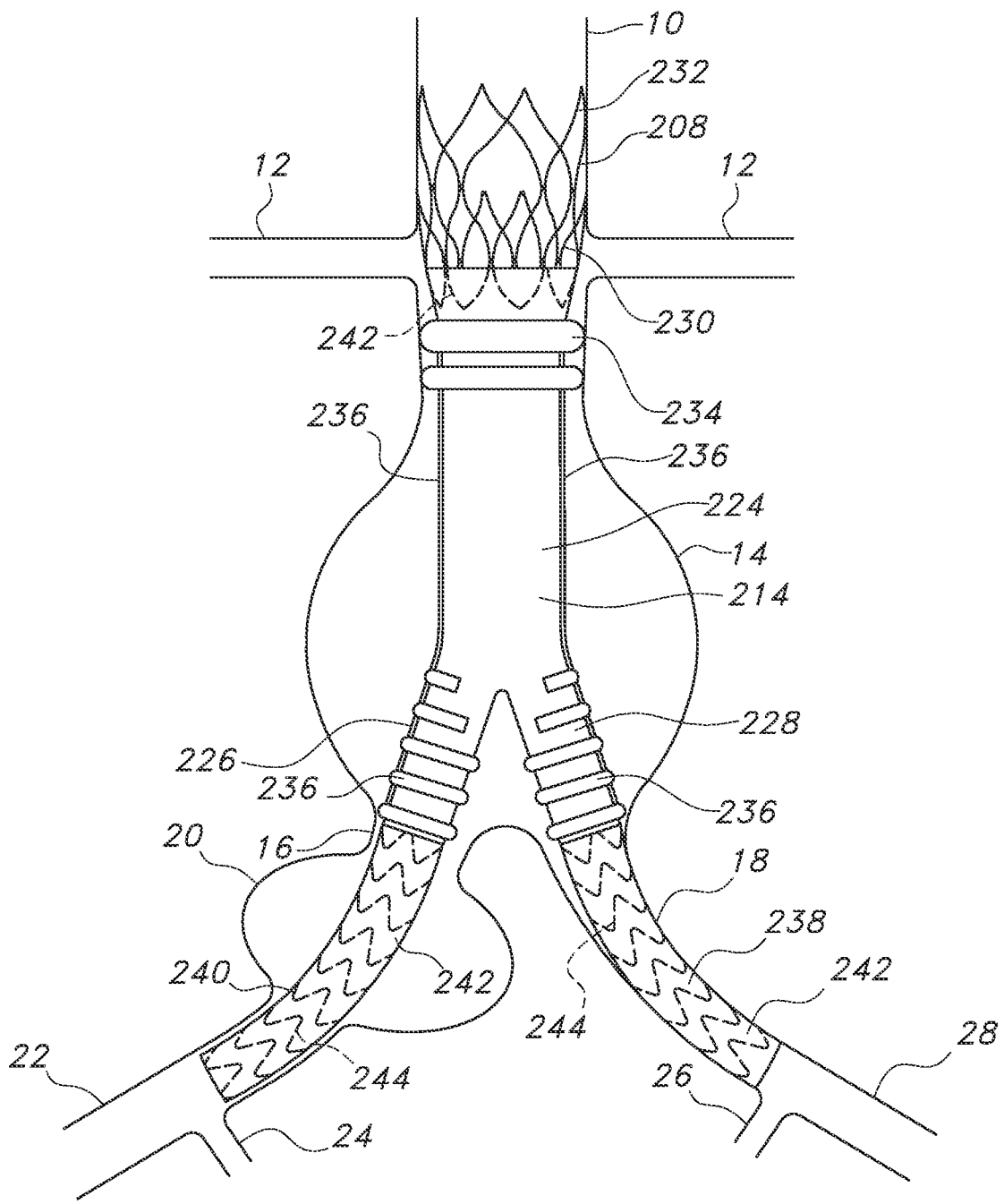
FIG. 29 depicts main body AAA device useful with the present invention.

As described above, the internal iliac preservation devices and methods of the present invention may be used in conjunction with a main body AAA device. A useful, but non-limiting AAA device is depicted below in FIG. 29.

A useful main body AAA device may include an inflatable graft 214. The inflatable graft 214 may be a bifurcated graft having a main graft body 224, an ipsilateral graft leg 226 and a contralateral graft leg 228. The inflatable graft 214 may further include a fill port (not shown) for an inflation medium (not shown). The distal portion 230 of stent 208 may be disposed to the main graft body 224 via a connector ring 242. The stent 208 and/or the connector ring 242 may be made from or include any biocompatible material, including metallic materials, such as but not limited to, nitinol (nickel titanium), cobalt-based alloy such as Elgiloy, platinum, gold, stainless steel, titanium, tantalum, niobium, and combinations thereof. The present invention, however, is not limited to the use of such a connector ring 242 and other shaped connectors for securing the distal portion 230 of the stent 208 at or near the end of the main graft body 224 may suitably be used. The proximal portion 232 of the stent 208 may include tissue engaging barbs (not shown) on the proximal portion 232 of the stent 208. Once the proximal stent 208 has been partially or fully deployed, the proximal inflatable cuff 234 may then be filled with inflation material, desirable a curable or hardenable material, which may serve to seal an outside surface of the inflatable cuff 234 to the inside surface of the vessel or aorta 10. The remaining network of inflatable channels 236 may also be filled with pressurized inflation material to provide a more rigid frame like structure to the inflatable graft 214. The device may also include a contralateral graft extension 238, as depicted in FIG. 20. The contralateral graft extension 238 is in an axial position which overlaps the contralateral leg 228 of the graft 214. The amount of desired overlap of the graft extension 238 with the contralateral leg 228 may vary depending on a variety of factors including vessel morphology, degree of vascular disease, patient status and the like. However, for some embodiments, the amount of axial overlap between the contralateral graft extension 238 and the contralateral leg 228 may be about 1 cm to about 5 cm; more specifically, about 2 cm to about 4 cm. Once the contralateral graft extension 238 has been deployed, an ipsilateral graft extension 240 may be similarly deployed in the ipsilateral graft leg 226. Graft extensions 238, 240, which may be interchangeable for some embodiments, or any other suitable extension devices or portions of the main graft section 224 may include a variety of suitable configurations. For some embodiments, graft extensions 238, 240 may include a polytetrafluoroethylene (PTFE) graft 242 with helical nitinol stent 244.

The above described stent-grafts 154, 156, if desired, may be deployable within the ipsilateral graft extension 240. Any of the above-described stent and/or graft materials may be used the inflatable graft 214, the stent 208, the connector ring 242, the contralateral graft extension 238 and the ipsilateral graft extension 240.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

The following embodiments or aspects of the invention may be combined in any fashion and combination and be within the scope of the present invention, as follows:

Embodiment 1. A system (100) for deploying a stent-graft at a branched artery comprising:
- a catheter (100) having a distal catheter portion (105) and a proximal catheter portion (107);
- a distal tip (102) disposed at the distal catheter portion (105);
- a first guidewire (118) having a proximal portion extending from the proximal catheter portion (107), a distal portion extendable through the distal tip (102) and a medial portion disposed between the proximal portion and the distal portion;
- a first outer sheath (104) slidably disposed over distal catheter portion (105);
- an integrated delivery system (111) disposed within the outer sheath (104) at the distal catheter portion (105), the integrated delivery system (111) comprising:
  - a second guidewire (122) having a proximal portion extending from the proximal catheter portion (107), a distal portion having a distal end portion (124) and a medial portion disposed between the proximal portion and the distal portion, the medial portion being slidably engaged with the first guidewire (118);
  - an expandable stent-graft (154) disposed over a lumen (126) of the second guidewire (122), the lumen (126) of the second guidewire (122) having a distal portion associated with the distal portion of the second guidewire (122) and an opposed proximal portion; and
  - a second outer sheath (128) disposed over the expandable stent-graft (154) and disposed over the lumen (126) of the second guidewire (122); and a slidable connector (132) slidably disposed over the medial portion of the first guidewire (118);
  - wherein the second guidewire (122) is slidably engaged with the slidable connector (132) to permit movement of the integrated second delivery system (111) along the first guidewire (118) when the first outer sheath (104) is retracted from distal catheter portion (105).

Embodiment 2. The system (100) of embodiment 1, wherein the expandable stent-graft (154) is a non-fenestrated stent-graft having no open passageways extending through a wall of the expandable stent-graft.

Embodiment 3. The system (100) of embodiment 1, wherein the slidable connector (132) has a hollow portion through which the first guidewire (118) is slidably disposed.

Embodiment 4. The system (100) of embodiment 2, wherein a portion of the medial portion of the second guidewire (122) is a looped portion, the looped portion being disposed proximal to the slidable connector (132).

Embodiment 5. The system (100) of embodiment 1, further comprising a sheath coupling (140) secured to a proximal portion of the second outer sheath (128) and slidably disposed over the first guidewire (118).

Embodiment 6. The system (100) of embodiment 5, wherein the first outer sheath (104) is slidably engagable with the sheath coupling (140) to move the second outer sheath (128) along the lumen (126) of the second guidewire (122).

Embodiment 7. The system (100) of embodiment 5, further comprising a rod (148) having a distal portion connected to the sheath coupling (140), the rod having a proximal portion disposed at the proximal catheter portion (107), whereby movement of the proximal portion of the rod (148) moves the second outer sheath (128) along the lumen (126) of the second guidewire (122).

Embodiment 8. The system (100) of embodiment 1, further comprising:
- a second distal tip (136) disposed at the distal portion of the lumen (126) of the second guidewire (122); and
- a thread (150) having a distal portion associated second distal tip (136), the thread (150) has a proximal accessible at the proximal catheter portion (107);
- whereby retraction of the thread (150) at the proximal catheter portion (107) moves the second distal tip (136) in a direction towards the second outer sheath (128).

Embodiment 9. The system (100) of embodiment 1, further comprising a second expandable stent-graft (156) deployable over the first guidewire (118).

Embodiment 10. The system (100) of embodiment 1, wherein the expandable stent-graft (154) comprises a self-expanding stent.

Embodiment 11. The system (100) of embodiment 9, wherein the second expandable stent-graft (156) and the expandable stent-graft (154) comprise self-expanding stents.

Embodiment 12. A method for deploying a stent-graft at a branched artery comprising:
- providing catheter system (100) comprising:
  - a catheter (100) having a distal catheter portion (105) and a proximal catheter portion (107);
  - a distal tip (102) disposed at the distal catheter portion (105);
  - a first guidewire (118) having a proximal portion extending from the proximal catheter portion (107), a distal portion extendable through the distal tip (102) and a medial portion disposed between the proximal portion and the distal portion;
  - a first outer sheath (104) slidably disposed over distal catheter portion (105);
  - an integrated delivery system (111) disposed within the outer sheath (104) at the distal catheter portion (107), the integrated delivery system (111) comprising:
    - a second guidewire (122) having a proximal portion extending from the proximal catheter portion (107), a distal portion having a distal end portion (124) and a medial portion disposed between the proximal portion and the distal portion, the medial portion being slidably engaged with the first guidewire (118);
    - an expandable stent-graft (154) disposed over a lumen (126) of the second guidewire (122), the lumen (126) of the second guidewire (122) having a distal portion associated with the distal portion of the second guidewire (122) and an opposed proximal portion;
    - a second outer sheath (128) disposed over the expandable stent-graft (154) and disposed over the lumen (126) of the second guidewire (122); and
    - a slidable connector (132) slidably disposed over the medial portion of the first guidewire (118);
    - wherein the second guidewire (122) is slidably engaged with the slidable connection (132);
- advancing the first guidewire (118) through a first body lumen (16, 22) having a branched bodily lumen (24) until the distal portion is beyond the branched bodily lumen (24);

retracting the first outer sheath (104) to uncover the integrated second delivery system (111);
advancing the slidable connector (132) until the second outer sheath (128) and the lumen (126) for the second guidewire (122) are disposed beyond the branched bodily lumen (24);
cannulating the branched artery (24) with the second guidewire (122);
retracting the slidable connector (132) to advance the second outer sheath (128) and the lumen (126) for the second guidewire (122) at least partially into the branched lumen (24);
retracting the second outer sheath (128);
deploying the expandable stent-graft (154) at least partially within the branched artery (24), wherein a distal portion (158) of the expandable stent-graft (154) is positioned within the branched artery (24);
retracting the second guidewire (122);
advancing the slidable connector (132) until the second outer sheath (128) and the lumen (126) for the second guidewire (122) are disposed within the first bodily lumen (16, 22); and
re-sheathing the integrated second delivery system (111) within the first outer sheath (104).

Embodiment 13. The method of embodiment 12, wherein at least a portion of the proximal portion (160) of the expandable stent-graft (154) is disposed within first bodily lumen (16, 22) before the branched bodily lumen (24).

Embodiment 14. The method of embodiment 12, further comprising: moving the second outer sheath (128) and the lumen (126) of the second guidewire (126) adjacently near the first guidewire (118) prior to the step of re-sheathing.

Embodiment 15. The method of embodiment 14, further comprising:
providing a snare (142) slidably disposed over the second outer sheath (128) and the first guidewire (118); and
pulling the snare (142) proximally.

Embodiment 16. The method of embodiment 14, further comprising:
providing a slidable sleeve (144) slidably disposed over the second outer sheath (126) and a pull wire (146) for the slidable sleeve (144); and
pulling the slidable sleeve (144) proximally.

Embodiment 17. The method of embodiment 12, further comprising:
withdrawing the integrated second delivery system (111) from the first bodily lumen (16, 22) while leaving the first guidewire (118) within the first bodily lumen (16, 22); and
deploying a second expandable stent (156) within the first bodily lumen (16, 22) so the first and second expandable stents (154, 156) sealing engage the wall of the first bodily lumen (16, 22).

Embodiment 18. A system (100) for deploying a stent-graft comprising:
a catheter (100) having a distal catheter portion (105) and a proximal catheter portion (107);
a distal tip (102) disposed at the distal catheter portion (105);
a first guidewire (118) having a proximal portion extending from the proximal catheter portion (107), a distal portion extendable through the distal tip (102) and a medial portion disposed between the proximal portion and the distal portion;
a second guidewire (122) having a proximal portion extending from the proximal catheter portion (107), a distal portion having a distal end portion (124) and a medial portion disposed between the proximal portion and the distal portion;
an expandable stent-graft disposed (154) over a lumen (126) of the second guidewire (122), the lumen (126) of the second guidewire (122) having a distal portion associated with the distal portion of the second guidewire (122) and an opposed proximal portion; and
an outer sheath (104) slidably disposed over distal catheter portion (105).

Embodiment 19. The system (100) of embodiment 18, further comprising a second outer sheath (128) disposed over the expandable stent-graft (154) and disposed over the lumen (126) of the second guidewire (122).

Embodiment 20. The system (100) of embodiment 18, wherein the expandable stent-graft (154) comprises a self-expanding stent or a balloon-expandable stent.

What is claimed is:

1. A method of deploying a graft comprising:
providing a system comprising:
a catheter having a distal catheter portion and a proximal catheter portion;
a first guidewire extending through the catheter; and
a first outer sheath disposed over the first guidewire;
providing a delivery system within the first outer sheath, the delivery system comprising:
a second guidewire;
an expandable stent or stent-graft disposed over a lumen of the second guidewire; and
a second outer sheath over the expandable stent or stent-graft;
placing the catheter superior to a vasculature bifurcation;
retracting the first outer sheath and cannulating a branch of the bifurcation with the second guidewire, such that the catheter is in the first bifurcation branch and the second guidewire is in the second bifurcation branch; and
retracting the second outer sheath to expand and deploy the expandable stent or stent-graft.

2. The method of claim 1, wherein the system further comprises a slidable connector configured to move along a portion of the first guidewire disposed between the first outer sheath and a distal tip of the catheter when the first outer sheath is retracted.

3. The method of claim 2, wherein the slidable connector is configured to allow the first guidewire to pass therethrough.

4. The method of claim 2, wherein a portion of the second guidewire is a looped portion, the looped portion being distal to the slidable connector.

5. The method of claim 2, wherein the slidable connector is disposed within the first outer sheath before retraction of the first outer sheath.

6. The method of claim 2, wherein the slidable connector is configured to move along the portion of the first guidewire to position the second guidewire into a branched artery.

7. The method of claim 1, wherein the system further comprises a stent securement component configured to keep the expandable stent-graft in a relatively fixed position over the second guidewire as the second outer sheath is retracted.

8. The method of claim 1, wherein the system comprises a second expandable stent-graft disposed over the first guidewire.

9. The method of claim 8, further comprising deploying the second stent graft in the first bifurcation branch.

10. The method of claim 9, wherein the first and second stent grafts are at least partially expanded against each other.

11. The method of claim 1, further comprising advancing the catheter proximally until the second guidewire is removed from the second bifurcation branch into the first bifurcation branch.

12. The method of claim 1, further comprising moving the delivery system towards the first guidewire.

13. The method of claim 12, further comprising re-sheathing the delivery system.

14. The method of claim 13, further comprising retracting the system from the vasculature.

15. The method of claim 12, wherein the system further comprises a thread associated with a distal tip of the delivery system, wherein the thread is configured to move the delivery system in the direction toward the first guidewire.

16. The method of claim 15, wherein the thread is disposed along the lumen of the second guidewire.

17. The method of claim 15, wherein the thread is disposed in a thread lumen.

18. The method of claim 12, wherein the system further comprises a slidable snare disposed over the second outer sheath, wherein the slidable snare is configured to move the delivery system in the direction toward the first guidewire.

19. The method of claim 1, further comprising retracting the second guidewire within the second outer sheath so that at least a portion of a distal tip of the second guidewire is recaptured within the second outer sheath.

20. The method of claim 1, wherein the system further comprises a slidable sleeve disposed over the second outer sheath, wherein the slidable sleeve is configured to move the delivery system in the direction toward the first guidewire.

* * * * *